United States Patent
Reader

(10) Patent No.: US 11,673,870 B2
(45) Date of Patent: *Jun. 13, 2023

(54) PHARMACEUTICAL COMPOUNDS

(71) Applicant: Sareum Limited, Pampisford (GB)

(72) Inventor: John Charles Reader, Linton (GB)

(73) Assignee: SAREUM LIMITED, Pampisford (GB)

( * ) Notice: Subject to any disclaimer, the term of this patent is extended or adjusted under 35 U.S.C. 154(b) by 132 days.

This patent is subject to a terminal disclaimer.

(21) Appl. No.: 17/108,266

(22) Filed: Dec. 1, 2020

(65) Prior Publication Data
US 2021/0087154 A1  Mar. 25, 2021

Related U.S. Application Data

(63) Continuation of application No. 16/351,620, filed on Mar. 13, 2019, now Pat. No. 10,882,829, which is a continuation of application No. 13/781,902, filed on Mar. 1, 2013, now abandoned.

(60) Provisional application No. 61/605,952, filed on Mar. 2, 2012.

(51) Int. Cl.
| C07D 263/48 | (2006.01) |
| A61P 29/00 | (2006.01) |
| A61P 17/06 | (2006.01) |
| A61P 37/06 | (2006.01) |
| C07D 413/12 | (2006.01) |

(52) U.S. Cl.
CPC .......... *C07D 263/48* (2013.01); *A61P 17/06* (2018.01); *A61P 29/00* (2018.01); *A61P 37/06* (2018.01); *C07D 413/12* (2013.01)

(58) Field of Classification Search
CPC .......... A61P 17/06; A61P 29/00; A61P 37/06; C07D 263/48; C07D 413/12
See application file for complete search history.

(56) References Cited

U.S. PATENT DOCUMENTS

| 7,125,891 | B2 | 10/2006 | Breslin et al. | |
| 8,378,095 | B2 | 2/2013 | Reader et al. | |
| 8,921,544 | B2 | 12/2014 | Reader et al. | |
| 9,187,465 | B2 | 11/2015 | Reader et al. | |
| 10,882,829 | B2 * | 1/2021 | Reader ................. | C07D 263/48 |
| 11,154,539 | B2 * | 10/2021 | Reader ................. | A61K 31/5377 |
| 2011/0166129 | A1 | 7/2011 | Machacek et al. | |
| 2013/0102592 | A1 | 4/2013 | Reader et al. | |
| 2013/0143915 | A1 | 6/2013 | Ellard et al. | |

FOREIGN PATENT DOCUMENTS

| DE | 2301030 | | 2/1974 |
| DE | 19653355 | A1 | 6/1998 |
| DK | 200600313 | L | 3/2006 |
| EP | 2634185 | A1 | 9/2013 |
| GB | 1374345 | | 11/1974 |
| GB | 1497536 | | 1/1978 |
| JP | 6310767 | A | 11/1994 |
| RU | 2011114992 | A | 10/2012 |
| SU | 623518 | | 9/1978 |
| WO | 2001058890 | A1 | 8/2001 |
| WO | 0200649 | A1 | 1/2002 |
| WO | 2004005283 | A1 | 1/2004 |
| WO | 2005040139 | A2 | 5/2005 |
| WO | 2006095159 | A1 | 9/2006 |
| WO | 2007043400 | A1 | 4/2007 |
| WO | 2007131953 | A1 | 11/2007 |
| WO | 2008024980 | A2 | 2/2008 |
| WO | 2008139161 | A1 | 11/2008 |
| WO | 2008156726 | A1 | 12/2008 |
| WO | 2009155156 | A1 | 12/2009 |
| WO | 2010005841 | A1 | 1/2010 |

(Continued)

OTHER PUBLICATIONS

Argiriadi et al., "Enabling Structure-Based Drug Design of Tyk2 Through Co-Crystallization with a Stabilizing Aminoindazole Inhibitor", BMC Structural Biology, Biomed Central Ltd., London GB, vol. 12, No. 1. Sep. 20, 2012.

European Search Report in European Application No. 13157419.6 (Publication No. 2634185). dated Jul. 1, 2013.

International Search Report in International Application No. PCT/EP2013/068198. dated Mar. 12, 2015.

Lykkeberg et al., "Preparation of Some 2,4-Disubstituted lmidazole-5-Carboxamides by Thermolysis of β-Substituted α-(1-Tetrazolyl) Acrylamides", Acta Chemica Scandinavica, Series B: Organic Chemistry and Biochemistry, B29(7), pp. 793-795. 1975.

(Continued)

*Primary Examiner* — Kara R McMillian
(74) *Attorney, Agent, or Firm* — Heslin Rothenberg Farley & Mesiti P.C.

(57) ABSTRACT

The invention provides a method of inhibiting a TYK2 kinase, which method comprises bringing into contact with the TYK2 kinase an effective TYK2 kinase-inhibiting amount of a compound having the formula (0):

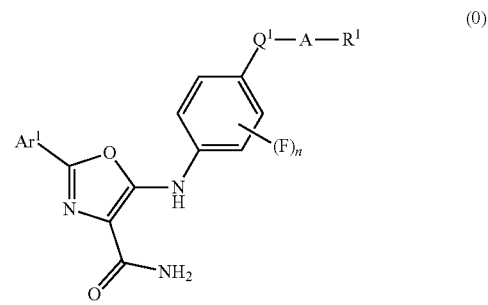

or a salt or stereoisomer thereof. The invention also provides a novel subset of compounds within formula (0) as well as pharmaceutical compositions containing them and their use in medicine.

20 Claims, No Drawings

(56) References Cited

FOREIGN PATENT DOCUMENTS

| WO | 2010011375 | A2 | 1/2010 |
|---|---|---|---|
| WO | 2010031835 | A2 | 3/2010 |
| WO | 2010055304 | A2 | 5/2010 |
| WO | 2011113802 | A2 | 9/2011 |
| WO | 2012000970 | A1 | 1/2012 |
| WO | 2012021611 | A1 | 2/2012 |
| WO | 2013055645 | A1 | 4/2013 |

OTHER PUBLICATIONS

Ozaki et al., "Syntheses of 5-Substitued Oxazole-4-Carboxylic Acid Derivatives with Inhibitory Activity on Blood Platelet Aggression", Chem. Pharm. Bull., 31(12), pp. 4417-4424. 1983.

Harrington et al., "VX-680, A Potent and Selective Small-Molecule Inhibitor of the Aurora Kinases, Suppresses Tumor Growth in vivo", Nature Medicine, vol. 10, No. 3, pp. 262-267. Mar. 2004.

Francheti et al., "Synthesis and Antitumor Activity of 2-β-D-Ribofuranosylozazole-4-carbozamide", (Oxazofurin), J. Med. Chem., 33, pp. 2849-2852. 1990.

Jansen et al., Some 4-Substituted Oxazoles, J. Chem. Soc., pp. 405-411. 1961.

Morwick et al. "Evolution of the Thienopyridine Class of Inhibitors of IκB Kinase-β: Part I: Hit-to-Lead Strategies", J. Med. Chem., 49, pp. 2898-2908. 2006.

Spiekermann et al., "The Protein Tyrosine Kinase Inhibitor SU5614 Inhibits FLT3 and Induces Growth Arrest and Apoptosis in AML-Derived Cell Lines Expressing a Constitutively Activated FLT3", Blood, 101(4), pp. 1494-1504. 2003.

Ponomarev et al., Zhurnal Fizicheskoi Khimii, 64(10), pp. 2723-2729 (Chem Abs. 114:100938). 1990.

Works et al., "Inhibition of TYK2 and JAK1 Ameliorates Imiquimod-lnduced Psoriasis-like Dermatitis by Inhibiting IL-22 and the IL-23/IL-17 Axis", The Journal of Immunology, vol. 193. Aug. 25, 2014.

\* cited by examiner

PHARMACEUTICAL COMPOUNDS

CROSS REFERENCE TO RELATED APPLICATION

This application is a continuation of U.S. application Ser. No. 16/351,620, filed Mar. 13, 2019, now allowed, which is a continuation application of U.S. application Ser. No. 13/781,902, filed Mar. 1, 2013, now abandoned, which claims priority of U.S. Provisional Application 61/605,952, filed Mar. 2, 2012. The entire contents of the prior applications are hereby incorporated herein by reference.

This invention relates to compounds that inhibit or modulate the activity of JAK kinases, in particular TYK2 kinase, and to the use of the compounds in the treatment or prophylaxis of disease states or conditions mediated by the kinases.

BACKGROUND OF THE INVENTION

Protein kinases constitute a large family of structurally related enzymes that are responsible for the control of a wide variety of signal transduction processes within the cell (Hardie and Hanks (1995) *The Protein Kinase Facts Book. I and II*, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks and Hunter, *FASEB J.*, (1995) 9.576-596; Knighton, et al., *Science*, (1991) 253, 407-414; Hiles, et al., *Cell*, (1992) 70, 419-429; Kunz, et al., *Cell*, (1993) 73, 585-596; Garcia-Bustos, et al., *EMBO J.*, (1994) 13, 2352-2361).

Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, disease and conditions of the immune system, disease and conditions of the central nervous system, and angiogenesis.

The Janus kinase (JAK) family is a family of intracellular non-receptor tyrosine kinases, ranging in size from 120-140 kDa, that transduce cytokine-mediated signals via the JAK-STAT pathway. The JAK family plays a role in the cytokine-dependent regulation of proliferation and function of cells involved in immune response. Currently, there are four known mammalian JAK family members: JAK1, JAK2, JAK3 and TYK2. JAK1, JAK2 and TYK2 are ubiquitously expressed whereas JAK3 is expressed in the myeloid and lymphoid lineages. The JAK family members are non-receptor tyrosine kinases that associate with many hematopoietin cytokines, receptor tyrosine kinases and GPCR's.

Each JAK kinase protein has a kinase domain and a catalytically inactive pseudo-kinase domain. The JAK proteins bind to cytokine receptors through their amino-terminal FERM (Band-4.1, ezrin, radixin, moesin) domains. After the binding of cytokines to their receptors, JAKs are activated and phosphorylate the receptors, thereby creating docking sites for signalling molecules, especially for members of the signal transducer and activator of transcription (STAT) family (Yamaoka et al, 2004. The Janus kinases (Jaks). Genome Biology 5(12): 253).

In mammals, JAK1, JAK2 and TYK2 are ubiquitously expressed. The role of TYK2 in the biological response to cytokines has been characterized using a mutant human cell line that was resistant to the effects of Type I interferons (IFNs) and by demonstrating that IFNa responsiveness could be restored by genetic complementation of TYK2 (Velazquez et al, 1992. Cell 70, 313-322). Further in vitro studies have implicated TYK2 in the signalling pathways of multiple other cytokines involved in both innate and adaptive immunity. However, analysis of TYK2$^{-/-}$ mice revealed less profound immunological defects than were anticipated (Karaghiosoff et al, 2000. Immunity 13, 549-560; Shimoda et al, 2000. Immunity 13, 561-671). Surprisingly, TYK2 deficient mice display merely reduced responsiveness to IFNα/β and signal normally to interleukin 6 (IL-6) and interleukin 10 (IL-10), both of which activate TYK2 in vitro. In contrast, TYK2 was shown to be essential for IL-12 signalling with the absence of TYK2 resulting in defective STAT4 activation and the failure of T cells from these mice to differentiate into IFNy-producing Th1 cells. Consistent with the involvement of TYK2 in mediating the biological effects of Type I IFNs and IL-12, TYK2$^{-/-}$ mice were more susceptible to viral and bacterial infections.

Thus far only a single patient with an autosomal recessive TYK2 deficiency has been described (Minegishi et al, 2006. Immunity 25, 745-755). The homozygous deletion of four base pairs (GCTT at nucleotide 550 in the TYK2 gene) and consequent frameshift mutation in the patient's coding DNA introduced a premature stop codon and resulted in the truncation of the TYK2 protein at amino acid 90. The phenotype of this null mutation in human cells was much more severe than predicted by the studies in murine cells lacking TYK2. The patient displayed clinical features reminiscent of the primary immunodeficiency hyper-IgE syndrome (HIES) including recurrent skin abscesses, atopic dermatitis, highly elevated serum IgE levels and susceptibility to multiple opportunistic infections.

Contrary to reports in TYK2$^{-/-}$ mice, signalling by a wide variety of cytokines was found to be impaired thus highlighting non-redundant roles for human TYK2 in the function of Type I IFNs, IL-6, IL-10, IL-12 and IL-23. An imbalance in T helper cell differentiation was also observed, with the patient's T cells exhibiting an extreme skew towards the development of IL-4 producing Th2 cells and impaired Th1 differentiation. Indeed, these cytokine signalling defects could be responsible for many of the clinical manifestations described, for example atopic dermatitis and elevated IgE levels (enhanced Th2), increased incidence of viral infections (IFN defect), infection with intracellular bacteria (IL-12/Th1 defect) and extracellular bacteria (IL-6 and IL-23/Th17 defect). Emerging evidence from genome-wide association studies suggests that single nucleotide polymorphisms (SNPs) in the TYK2 gene significantly influence autoimmune disease susceptibility.

Less efficient TYK2 variants are associated with protection against systemic lupus erythematosus (SLE) (TYK2 rs2304256 and rsl2720270, Sigurdsson et al, 2005. Am. J. Hum. Genet. 76, 528-537; Graham et al, 2007. Rheumatology 46, 927-930; Hellquist et al, 2009. J. Rheumatol. 36, 1631-1638; Jarvinen et al, 2010. Exp. Dermatol. 19, 123-131) and multiple sclerosis (MS) (rs34536443, Ban et al, 2009. Eur. J. Hum. Genet. 17, 1309-1313; Mero et al, 2009. Eur. J. Hum. Genet. 18, 502-504), whereas predicted gain-of-function mutations increase susceptibility to inflammatory bowel disease (IBD) (rs280519 and rs2304256, Sato et al, 2009. J. Clin. Immunol. 29, 815-825).

In support of the involvement of TYK2 in immunopathologic disease processes, it has been shown that B10.D1 mice harbouring a missense mutation in the pseudokinase domain of TYK2 that results in the absence of encoded TYK2 protein are resistant to both autoimmune arthritis (CIA) and experimental autoimmune encephalomyelitis (EAE) (Shaw et al, 2003. PNAS 100, 11594-11599; Spach et al, 2009. J. Immunol. 182, 7776-7783). Furthermore, a recent study showed that TYK2$^{-/-}$ mice were completely resistant to MOG-induced EAE (Oyamada et al, 2009. J. Immunol. 183, 7539-7546). In these mice resistance was accompanied by a lack of CD4 T cells infiltrating the spinal cord, a failure to signal through IL-12R and IL-23R and hence the inability to upregulate encephalitogenic levels of IFNy and IL-17.

The non-receptor tyrosine kinase TYK2 plays essential roles in both innate and adaptive immunity. A lack of TYK2 expression manifests in the attenuated signalling of multiple proinflammatory cytokines and a profound imbalance in T helper cell differentiation. Furthermore, evidence from genetic association studies supports that TYK2 is a shared autoimmune disease susceptibility gene. Taken together, these reasons suggest TYK2 as a target for the treatment of inflammatory and auto-immune diseases.

Overexpression of TYK2 kinase has been implicated in the development of some disease states. For example, elevated levels of TYK2 were found in patients suffering from progressive pulmonary sarcoidosis (Schischmanoff et al., *Sarcoidosis Vasc. Diffuse.*, 2006, 23(2), 101-7).

Several JAK family inhibitors have been reported in the literature which may be useful in the medical field (Ghoreschi et al, 2009. Immunol Rev, 228:273-287). It is expected that a selective TYK2 inhibitor that inhibits TYK2 with greater potency than JAK2 may have advantageous therapeutic properties, because inhibition of JAK2 can cause anemia (Ghoreschi et al, 2009. Nature Immunol. 4, 356-360).

Even though TYK2 inhibitors are known in the art there is a need for providing additional TYK2 inhibitors having at least partially more effective pharmaceutically relevant properties, like activity, selectivity especially over JAK2 kinase, and ADMET properties. Thus, an object of the present invention is to provide a new class of compounds as TYK2 inhibitors which preferably show selectivity over JAK2 and may be effective in the treatment or prophylaxis of disorders associated with TYK2.

WO2012/000970 (Cellzome) discloses a series of triazolopyridines as TYK2 kinase inhibitors. WO2011/113802 (Roche) discloses a series of imidazopyridines as TYK2 kinase inhibitors. The properties of JAK kinases and their relevance as therapeutic targets are also disclosed in WO2008/156726, WO2009/155156, WO2010/005841 and WO2010/011375, all in the name of Merck.

WO2010/055304 (Sareum) discloses a family of substituted oxazole carboxamides for use in the prophylaxis or treatment of autoimmune diseases and in particular multiple sclerosis. The compounds disclosed in WO2010/055304 are described as being FLT3 kinase inhibitors. The kinase inhibiting effect of oxazole carboxamides is also disclosed in International patent application WO2008/139161 (Sareum).

SUMMARY OF THE INVENTION

It has now been found that a subgroup of compounds of the type disclosed in WO2008/139161 and WO2010/055304 are particularly effective inhibitors of TYK2 kinase and, furthermore, demonstrate selectivity against TYK2 compared to the other three JAK kinases JAK1, JAK2 and JAK3. Such compounds therefore provide a means of treating inflammatory conditions and diseases whilst exhibiting reduced or substantially no side effects associated with JAK1, JAK2 or JAK3 inhibition.

Accordingly, in a first embodiment (Embodiment 1.0), the invention provides a method of inhibiting a TYK2 kinase, which method comprises bringing into contact with the TYK2 kinase an effective TYK2 kinase-inhibiting amount of a compound having the formula (0):

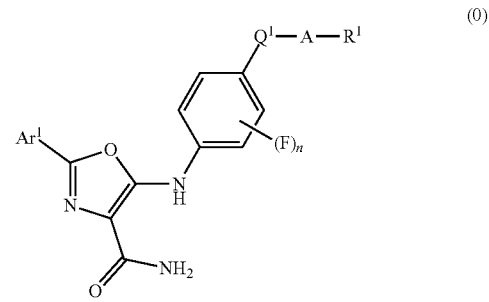

or a salt or stereoisomer thereof; wherein:

n is 0, 1 or 2;

Ar$^1$ is selected from phenyl, pyridyl, thienyl and furanyl, each of which is optionally substituted with one, two or three substituents independently selected from halogen, C$_{1-4}$ alkyl, hydroxyl-C$_{1-4}$ alkyl, C$_{1-2}$ alkoxy-C$_{1-4}$ alkyl, C$_{1-4}$ alkoxy, C$_{1-2}$ alkoxy-C$_{1-4}$ alkoxy, C$_{2-4}$ alkenyl, C$_{2-4}$ alkenyloxy, C$_{2-4}$ alkynyl, C$_{2-4}$ alkynyloxy, cyano, C$_{1-4}$ alkanoyl, hydroxy and C$_{1-4}$ alkanoyloxy, wherein the C$_{1-4}$ alkyl and C$_{1-4}$ alkoxy moieties are each optionally substituted with one or more fluorine atoms;

Q$^1$ is selected from C(=O), S(=O) and SO$_2$;

A is absent or is NR$^2$;

R$^1$ is selected from:

hydrogen;

a C$_{1-6}$ non-aromatic hydrocarbon group optionally substituted with one or more substituents selected from hydroxyl, C$_{1-2}$ alkoxy, amino, mono-C$_{1-4}$ alkylamino, di-C$_{1-4}$ alkylamino, 3- to 7-membered non-aromatic carbocyclic and heterocyclic rings containing one or two heteroatom ring members selected from O, N and S, and bridged bicyclic heterocyclic rings of seven to nine ring members of which one or two are nitrogen atoms, the carbocyclic and heterocyclic rings and bridged bicyclic heterocyclic rings being optionally substituted with one or more hydroxy, C$_{1-4}$ alkyl, C$_{1-4}$ alkoxy, C$_{1-4}$ alkanoyl, C$_{1-4}$ alkanoyloxy, C$_{1-4}$ alkoxycarbonyl or hydroxyl-C$_{1-3}$ alkyl groups; and 3- to 7-membered non-aromatic carbocyclic and heterocyclic rings containing one or two heteroatom ring members selected from O, N and S, and bridged bicyclic heterocyclic rings of seven to nine ring members of which one or two are nitrogen atoms, the carbocyclic and heterocyclic rings and bridged bicyclic heterocyclic rings being optionally substituted with one or more hydroxy, $C_{1-4}$ alkyl, $C_{1-4}$ alkoxy, $C_{1-4}$ alkanoyl, $C_{1-4}$ alkanoyloxy, $C_{1-4}$ alkoxycarbonyl, amino-$C_{1-3}$alkyl, mono-$C_{1-2}$ alkylamino-$C_{1-3}$ alkyl, di-$C_{1-2}$ alkylamino-$C_{1-3}$ alkyl or hydroxyl-$C_{1-3}$ alkyl groups;

$R^2$ is selected from hydrogen and $C_{1-4}$ alkyl; or $NR^1R^2$ forms a 4- to 7-membered non-aromatic nitrogen-containing heterocyclic ring optionally containing a second heteroatom ring member selected from nitrogen and oxygen, the heterocyclic ring being optionally substituted with one or more hydroxy, $C_{1-4}$ alkyl, $C_{1-4}$ alkanoyl, $C_{1-4}$ alkanoyloxy, $C_{1-4}$ alkoxy, $C_{1-4}$ alkoxycarbonyl amino-$C_{1-3}$alkyl, mono-$C_{1-2}$ alkylamino-$C_{1-3}$ alkyl, di-$C_{1-2}$ alkylamino-$C_{1-3}$ alkyl or hydroxy-$C_{1-3}$ alkyl groups.

Within formula (0), n may be selected from 0 and 1 (Embodiment 1.0A), or n may be 0 (Embodiment 1.0B) or n may be 1 (Embodiment 1.0C).

In a second embodiment (Embodiment 1.1), the invention provides a method of inhibiting a TYK2 kinase, which method comprises bringing into contact with the TYK2 kinase an effective TYK2 kinase-inhibiting amount of a compound having the formula (1):

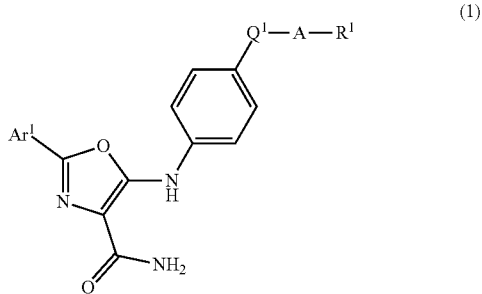

(1)

or a salt or stereoisomer thereof; wherein:

$Ar^1$ is selected from phenyl, pyridyl, thienyl and furanyl, each of which is optionally substituted with one, two or three substituents independently selected from halogen, $C_{1-4}$ alkyl, hydroxyl-$C_{1-4}$ alkyl, $C_{1-2}$ alkoxy-$C_{1-4}$ alkyl, $C_{1-4}$ alkoxy, $C_{1-2}$ alkoxy-$C_{1-4}$ alkoxy, $C_{2-4}$ alkenyl, $C_{2-4}$ alkenyloxy, $C_{2-4}$ alkynyl, $C_{2-4}$ alkynyloxy, cyano, $C_{1-4}$ alkanoyl, hydroxy and $C_{1-4}$ alkanoyloxy, wherein the $C_{1-4}$ alkyl and $C_{1-4}$ alkoxy moieties are each optionally substituted with one or more fluorine atoms;

$Q^1$ is selected from C(=O), S(=O) and $SO_2$;

A is absent or is $NR^2$;

$R^1$ is selected from:

hydrogen;

a $C_{1-6}$ non-aromatic hydrocarbon group optionally substituted with one or more substituents selected from hydroxyl, $C_{1-2}$ alkoxy, amino, mono-$C_{1-4}$ alkylamino, di-$C_{1-4}$ alkylamino, 3- to 7-membered non-aromatic carbocyclic and heterocyclic rings containing one or two heteroatom ring members selected from O, N and S, and bridged bicyclic heterocyclic rings of seven to nine ring members of which one or two are nitrogen atoms, the carbocyclic and heterocyclic rings and bridged bicyclic heterocyclic rings being optionally substituted with one or more hydroxy, $C_{1-4}$ alkyl, $C_{1-4}$ alkoxy, $C_{1-4}$ alkanoyl, $C_{1-4}$ alkanoyloxy, $C_{1-4}$ alkoxycarbonyl or hydroxyl-$C_{1-3}$ alkyl groups; and 3- to 7-membered non-aromatic carbocyclic and heterocyclic rings containing one or two heteroatom ring members selected from O, N and S, and bridged bicyclic heterocyclic rings of seven to nine ring members of which one or two are nitrogen atoms, the carbocyclic and heterocyclic rings and bridged bicyclic heterocyclic rings being optionally substituted with one or more hydroxy, $C_{1-4}$ alkyl, $C_{1-4}$ alkoxy, $C_{1-4}$ alkanoyl, $C_{1-4}$ alkanoyloxy, $C_{1-4}$ alkoxycarbonyl, amino-$C_{1-3}$alkyl, mono-$C_{1-2}$ alkylamino-$C_{1-3}$ alkyl, di-$C_{1-2}$ alkylamino-$C_{1-3}$ alkyl or hydroxyl-$C_{1-3}$ alkyl groups;

$R^2$ is selected from hydrogen and $C_{1-4}$ alkyl; or $NR^1R^2$ forms a 4- to 7-membered non-aromatic nitrogen-containing heterocyclic ring optionally containing a second heteroatom ring member selected from nitrogen and oxygen, the heterocyclic ring being optionally substituted with one or more hydroxy, $C_{1-4}$ alkyl, $C_{1-4}$ alkanoyl, $C_{1-4}$ alkanoyloxy, $C_{1-4}$ alkoxy, $C_{1-4}$ alkoxycarbonyl amino-$C_{1-3}$alkyl, mono-$C_{1-2}$ alkylamino-$C_{1-3}$ alkyl, di-$C_{1-2}$ alkylamino-$C_{1-3}$ alkyl or hydroxy-$C_{1-3}$ alkyl groups.

Particular and preferred aspects and embodiments of the invention are set out below in Embodiments 1.2 to 2.26 and 3.1 to 3.3.

1.2 A method according to any one of Embodiments 1.0 to 1.1 wherein $Ar^1$ is optionally substituted phenyl.

1.3 A method according to any one of Embodiments 1.0 to 1.1 wherein $Ar^1$ is optionally substituted pyridyl.

1.4 A method according to any one of Embodiments 1.0 to 1.1 wherein $Ar^1$ is optionally substituted thienyl.

1.5 A method according to any one of Embodiments 1.0 to 1.1 wherein $Ar^1$ is optionally substituted furanyl 1.6 A method according to any one of Embodiments 1.0 to 1.5 wherein the optional substituents for $Ar^1$ are independently selected from halogen, $C_{1-4}$ alkyl, hydroxy-$C_{1-4}$ alkyl, $C_{1-2}$ alkoxy-$C_{1-4}$ alkyl, $C_{1-4}$ alkoxy, $C_{1-2}$ alkoxy-$C_{1-4}$ alkoxy, $C_{2-4}$ alkenyl, $C_{2-4}$ alkenyloxy, $C_{2-4}$ alkynyl, $C_{2-4}$ alkynyloxy, cyano, $C_{1-4}$ alkanoyl, hydroxy and $C_{1-4}$ alkanoyloxy, wherein the $C_{1-4}$ alkyl and $C_{1-4}$ alkoxy moieties are each optionally substituted with one or more fluorine atoms.

1.7 A method according to Embodiment 1.6 wherein the optional substituents for $Ar^1$ are independently selected from halogen, $C_{1-3}$ alkyl, hydroxy-$C_{1-3}$ alkyl, $C_{1-2}$ alkoxy-$C_{1-3}$ alkyl, $C_{1-3}$ alkoxy, $C_{1-2}$ alkoxy-$C_{1-3}$ alkoxy, cyano, $C_{1-3}$ alkanoyl and $C_{1-3}$ alkanoyloxy, wherein the $C_{1-3}$ alkyl and $C_{1-3}$ alkoxy moieties are each optionally substituted with one or more fluorine atoms.

1.8 A method according to Embodiment 1.7 wherein the optional substituents for $Ar^1$ are independently selected from fluorine, chlorine, bromine, $C_{1-3}$ alkyl, hydroxy-$C_{1-3}$ alkyl, methoxy-$C_{1-3}$ alkyl, $C_{1-3}$-alkoxy, methoxy-$C_{1-3}$ alkoxy, cyano, $C_{1-3}$ alkanoyl and $C_{1-3}$ alkanoyloxy, wherein the $C_{1-3}$ alkyl and $C_{1-3}$ alkoxy moieties are each optionally substituted with one or more fluorine atoms.

1.9 A method according to Embodiment 1.8 wherein the optional substituents for $Ar^1$ are independently selected from fluorine, chlorine, bromine, methyl, ethyl, isopropyl, hydroxymethyl, hydroxyethyl, methoxyethyl, methoxy, ethoxy, isopropoxy, methoxyethoxy, cyano, acetyl, acetoxy, trifluoromethyl, trifluoromethoxy, difluoromethyl and difluoromethoxy.

1.10 A method according to Embodiment 1.9 wherein the optional substituents for $Ar^1$ are independently selected from fluorine, chlorine, methyl, ethyl, isopropyl, hydroxymethyl, methoxy, ethoxy, isopropoxy, cyano, acetyl, acetoxy, trifluoromethyl, trifluoromethoxy, difluoromethyl and difluoromethoxy.

1.11 A method according to Embodiment 1.10 wherein the optional substituents for $Ar^1$ are independently selected from fluorine, chlorine, methyl, ethyl, methoxy, cyano, acetyl and trifluoromethyl.

1.12 A method according to Embodiment 1.11 wherein the optional substituents for $Ar^1$ are independently selected from fluorine and chlorine.

1.13 A method according to Embodiment 1.12 wherein each substituent is fluorine.

1.14 A method according to any one of Embodiments 1.1 to 1.13 wherein $Ar^1$ is unsubstituted or has 1, 2 or 3 substituents.

1.15 A method according to Embodiment 1.14 wherein $Ar^1$ is unsubstituted.

1.16 A method according to Embodiment 1.14 wherein $Ar^1$ has 1 substituent.

1.17 A method according to Embodiment 1.14 wherein $Ar^1$ has 2 substituents.

1.18 A method according to Embodiment 1.14 wherein $Ar^1$ has 3 substituents.

1.19 A method according to Embodiment 1.14 wherein $Ar^1$ is unsubstituted or has 1 or 2 substituents.

1.20 A method according to any one of Embodiments 1.0 to 1.1, 1.2 and 1.6 to 1.17 wherein $Ar^1$ is an unsubstituted phenyl group or a 2-monosubstituted, 3-monosubstituted, 4-monosubstituted, 2,3 disubstituted, 2,4 disubstituted, 2,5 disubstituted or 2,6 disubstituted phenyl group.

1.21 A method according to Embodiment 1.20 wherein $Ar^1$ is selected from unsubstituted phenyl, 2-fluorophenyl, 2-hydroxyphenyl, 2-methoxyphenyl, 2-methylphenyl, 3-fluorophenyl, 3-methoxyphenyl, 2,6-difluorophenyl, 2-fluoro-3-methoxyphenyl, 2-fluoro-5-methoxyphenyl, 2-chloro-6-methoxyphenyl, 2-fluoro-6-methoxyphenyl, 2,6-dichlorophenyl, 2-chloro-6-fluorophenyl, and 5-fluoro-2-methoxyphenyl.

1.22 A method according to Embodiment 1.21 wherein $Ar^1$ is selected from 2,6-difluorophenyl, 2-chloro-6-fluorophenyl and 2,6-dichlorophenyl.

1.23 A method according to Embodiment 1.22 wherein $Ar^1$ is 2,6-difluorophenyl.

1.23A A method according to Embodiment 1.22 wherein $Ar^1$ is 2-chloro-6-fluorophenyl.

1.23B A method according to Embodiment 1.22 wherein $Ar^1$ is 2,6-dichlorophenyl.

1.24 A method according to any one of Embodiments 1.0 to 1.23B wherein $Q^1$ is C(=O).

1.25 A method according to any one of Embodiments 1.0 to 1.23B wherein $Q^1$ is S(=O).

1.26 A method according to any one of Embodiments 1.0 to 1.23B wherein $Q^1$ is $SO_2$.

1.27 A method according to any one of Embodiments 1.0 to 1.26 wherein A is absent (i.e. the moieties $R^1$ and $Q^1$ are directly joined together)

1.28 A method according to any one of Embodiments 1.0 to 1.23B wherein A is absent and $Q^1$ is $SO_2$.

1.29 A method according to any one of Embodiments 1.0 to 1.26 wherein A is $NR^2$.

1.30 A method according to any one of Embodiments 1.0 to 1.29 wherein $R^1$ is selected from:
hydrogen;
a $C_{1-6}$ saturated hydrocarbon group optionally substituted with one or more substituents selected from hydroxy, $C_{1-2}$ alkoxy, amino, mono-$C_{1-4}$ alkylamino, di-$C_{1-4}$ alkylamino, 3- to 6-membered saturated carbocyclic rings and 4 to 7 membered heterocyclic rings containing one or two heteroatom ring members selected from O, N and S, and bridged bicyclic heterocyclic rings of seven to nine ring members of which one or two are nitrogen atoms, the carbocyclic and heterocyclic rings and bridged bicyclic heterocyclic rings being optionally substituted with one or more hydroxy, $C_{1-4}$ alkyl, $C_{1-4}$ alkoxy, $C_{1-4}$ alkanoyl, $C_{1-4}$ alkanoyloxy, $C_{1-4}$ alkoxycarbonyl, amino-$C_{1-3}$ alkyl, mono-$C_{1-2}$ alkylamino-$C_{1-3}$ alkyl, di-$C_{1-2}$ alkylamino-$C_{1-3}$ alkyl or hydroxy-$C_{1-3}$ alkyl groups; and 3- to 6-membered saturated carbocyclic rings and 4 to 7 membered heterocyclic rings containing one or two heteroatom ring members selected from O, N and S, and bridged bicyclic heterocyclic rings of seven to nine ring members of which one or two are nitrogen atoms, the carbocyclic and heterocyclic rings and bridged bicyclic heterocyclic rings being optionally substituted with one or more hydroxy, $C_{1-4}$ alkyl, $C_{1-4}$ alkoxy, $C_{1-4}$ alkanoyl, $C_{1-4}$ alkanoyloxy, $C_{1-4}$ alkoxycarbonyl, amino-$C_{1-3}$ alkyl, mono-$C_{1-2}$ alkylamino-$C_{1-3}$ alkyl, di-$C_{1-2}$ alkylamino-$C_{1-3}$ alkyl or hydroxy-$C_{1-3}$ alkyl groups;

$R^2$, when present, is selected from hydrogen and $C_{1-4}$ alkyl; or $NR^1R^2$ forms a 4- to 7-membered saturated nitrogen-containing heterocyclic ring optionally containing a second heteroatom ring member selected from nitrogen and oxygen, the heterocyclic ring being optionally substituted with one or more hydroxy, $C_{1-4}$ alkyl, $C_{1-4}$ alkanoyl, $C_{1-4}$ alkanoyloxy, $C_{1-4}$ alkoxy, $C_{1-4}$ alkoxycarbonyl or hydroxy-$C_{1-3}$ alkyl groups.

1.31 A method according to Embodiment 1.30 wherein $R^1$ is selected from:
hydrogen;
a $C_{1-4}$ alkyl group optionally substituted with one or more substituents selected from hydroxyl, $C_{1-3}$ alkoxy, amino, mono-$C_{1-3}$ alkylamino, di-$C_{1-3}$ alkylamino, 3- to 5-membered saturated carbocyclic rings and 4- to 6-membered heterocyclic rings containing one or two heteroatom ring members selected from O, N and S, the carbocyclic and heterocyclic rings being optionally substituted with one or more hydroxy, $C_{1-3}$ alkyl, $C_{1-3}$ alkoxy, $C_{1-3}$ alkanoyl, $C_{1-3}$ alkanoyloxy, $C_{1-3}$ alkoxycarbonyl, or hydroxy-$C_{1-3}$ alkyl groups; and 3- to 5-membered saturated carbocyclic rings and 4 to 6 membered heterocyclic rings containing one or two heteroatom ring members selected from O, N and S, the carbocyclic and heterocyclic rings being optionally substituted with one or more hydroxy, $C_{1-3}$ alkyl, $C_{1-3}$ alkoxy, $C_{1-3}$ alkanoyl, $C_{1-3}$ alkanoyloxy, $C_{1-4}$ alkoxycarbonyl or hydroxy-$C_{1-3}$ alkyl groups;

$R^2$, when present, is selected from hydrogen and $C_{1-2}$ alkyl; or $NR^1R^2$ forms a 4- to 7-membered saturated nitrogen-containing heterocyclic ring optionally containing a second heteroatom ring member selected from nitrogen and oxygen, the heterocyclic ring being optionally substituted with one or more hydroxy, $C_{1-3}$ alkyl, $C_{1-3}$ alkanoyl, $C_{1-3}$ alkanoyloxy, $C_{1-3}$ alkoxy, $C_{1-4}$ alkoxycarbonyl or hydroxy-$C_{1-3}$ alkyl groups.

1.31 A method according to Embodiment 1.30 wherein $R^1$ is selected from:
hydrogen;
a $C_{1-4}$ alkyl group optionally substituted with one or more substituents selected from hydroxy, amino, mono-$C_{1-3}$ alkylamino and di-$C_{1-3}$ alkylamino; and 5 to 6-membered heterocyclic rings containing a nitrogen ring member and optionally a second ring member selected from N and O, the heterocyclic rings being optionally substituted with one or more $C_{1-3}$ alkyl or hydroxy-$C_{1-3}$ alkyl groups;

$R^2$, when present, is selected from hydrogen and $C_{1-2}$ alkyl; or $NR^1R^2$ forms a 5 to 6-membered heterocyclic ring containing a nitrogen ring member and optionally a second ring member selected from N and O, the heterocyclic rings being optionally substituted with one or more $C_{1-3}$ alkyl or hydroxy-$C_{1-3}$ alkyl groups.

1.32 A method according to Embodiment 1.31 wherein $R^1$ is selected from:

hydrogen;

a $C_{1-4}$ alkyl group optionally substituted with one or more substituents selected from hydroxy, amino and mono-$C_{1-3}$ alkylamino; and 5 to 6-membered heterocyclic rings selected from pyrrolidine, piperidine, piperazine and morpholine, the heterocyclic rings being optionally substituted with one or more $C_{1-3}$ alkyl or hydroxy-$C_{1-3}$ alkyl groups;

$R^2$, when present, is selected from hydrogen and $C_{1-2}$ alkyl; or $NR^1R^2$ forms a 5 to 6-membered heterocyclic ring selected from pyrrolidine, piperidine, piperazine and morpholine, the heterocyclic ring being optionally substituted with one or more $C_{1-3}$ alkyl or hydroxy-$C_{1-3}$ alkyl groups.

1.33 A method according to Embodiment 1.32 wherein $R^1$ is selected from:

hydrogen;

a $C_{1-3}$ alkyl group optionally substituted with one or more substituents selected from hydroxy, amino and methylamino; and 5 to 6-membered heterocyclic rings selected from pyrrolidine, piperidine, piperazine and morpholine, the heterocyclic rings being optionally substituted with one or more $C_{1-3}$ alkyl or hydroxy-$C_{1-3}$ alkyl groups;

$R^2$, when present, is selected from hydrogen and $C_{1-2}$ alkyl; or $NR^1R^2$ forms a 5 to 6-membered heterocyclic ring selected from pyrrolidine, piperidine, piperazine and morpholine, the heterocyclic ring being optionally substituted with one or more $C_{1-3}$ alkyl or hydroxy-$C_{1-3}$ alkyl groups.

1.34 A method according to Embodiment 1.33 wherein $R^1$ is selected from:

hydrogen;

a $C_{1-3}$ alkyl group optionally substituted with one or more substituents selected from hydroxy, amino and methylamino; and 5 to 6-membered heterocyclic rings selected from pyrrolidine and piperidine, the heterocyclic rings being optionally substituted with a methyl group;

$R^2$, when present, is selected from hydrogen and methyl; or $NR^1R^2$ forms a 5 to 6-membered heterocyclic ring selected from pyrrolidine and morpholine, the heterocyclic ring being optionally substituted with a hydroxymethyl group.

1.35 A method according to Embodiment 1.34 wherein $Q^1$-A-$R^1$ is selected from groups AA to AR in the table below:

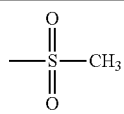   AA

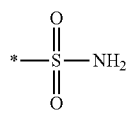   AB

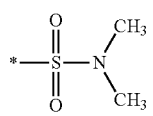   AC

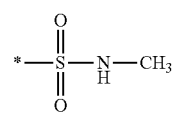   AD

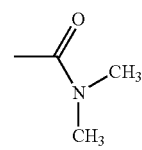   AE

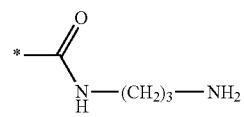   AF

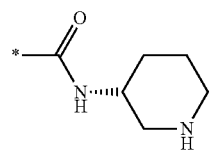   AG

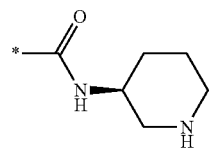 [SMILES: *C(=O)N[C@H]1CCCNC1]   AH

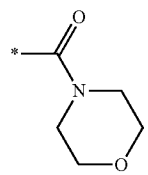 [SMILES: *C(=O)N1CCOCC1]   AI

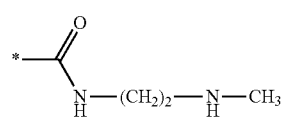   AJ

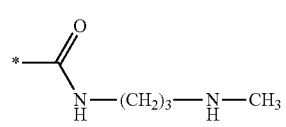   AK

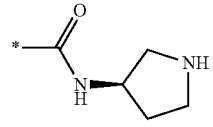 [SMILES: *C(=O)N[C@@H]1CCNC1]   AL

-continued

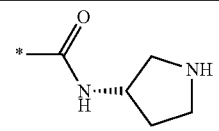 AM

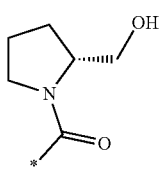 [SMILES: *C(=O)N1CCC[C@@H]1CO] AN

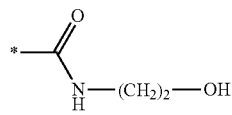 AO

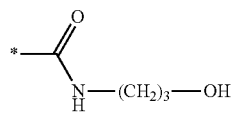 AP

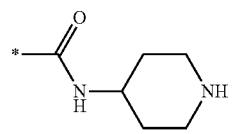 [SMILES: *C(=O)NC1CCNCC1] AQ

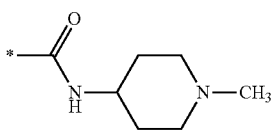 [SMILES: *C(=O)NC1CCN(C)CC1] AR wherein the point of attachment to the phenyl group is indicated by the asterisk.

1.36 A method according to Embodiment 1.35 wherein $Q^1$-A-$R^1$ is the group AA.

1.37 A method according to Embodiment 1.0 or 1.1 wherein the compound of formula (0) or (1) is selected from:

2-(2,6-difluorophenyl)-5-(4-(methylsulfonyl)phenylamino)oxazole-4-carboxamide;

2-(2,6-difluorophenyl)-5-(4-sulfamoylphenylamino)oxazole-4-carboxamide;

2-(2,6-difluorophenyl)-5-(4-(N,N-dimethylsulfamoyl)phenylamino)oxazole-4-carboxamide;

2-(2,6-difluorophenyl)-5-(4-(N'-methylsulfamoyl)phenylamino)oxazole-4-carboxamide;

2-(2,6-difluorophenyl)-5-(4-(dimethylcarbamoyl)phenylamino)oxazole-4-carboxamide;

5-(4-((3-aminopropyl)carbamoyl)phenylamino)-2-(2,6-difluorophenyl)oxazole-4-carboxamide;

(R)-2-(2,6-difluorophenyl)-5-(4-(piperidin-3-ylcarbamoyl)phenylamino)oxazole-4-carboxamide;

(S)-2-(2,6-difluorophenyl)-5-(4-(piperidin-3-ylcarbamoyl)phenylamino)oxazole-4-carboxamide;

2-(2,6-difluorophenyl)-5-(4-(morpholine-4-carbonyl) phenylamino)oxazole-4-carboxamide;

5-(4-((2-(methylamino)ethyl)carbamoyl)phenylamino)-2-(2,6-difluorophenyl) oxazole-4-carboxamide;

5-(4-((3-(methylamino)propyl)carbamoyl)phenylamino)-2-(2,6-difluorophenyl) oxazole-4-carboxamide;

(R)-2-(2,6-difluorophenyl)-5-(4-(pyrrolidin-3-ylcarbamoyl)phenylamino)oxazole-4-carboxamide;

(S)-2-(2,6-difluorophenyl)-5-(4-(pyrrolidin-3-ylcarbamoyl)phenylamino)oxazole-4-carboxamide;

(R)-2-(2,6-difluorophenyl)-5-(4-(2-(hydroxymethyl)pyrrolidine-1-carbonyl) phenylamino)oxazole-4-carboxamide;

5-(4-((2-hydroxyethyl)carbamoyl)phenylamino)-2-(2,6-difluorophenyl)oxazole-4-carboxamide;

5-(4-((3-hydroxypropyl)carbamoyl)phenylamino)-2-(2,6-difluorophenyl)oxazole-4-carboxamide;

2-(2,6-difluorophenyl)-5-(4-(piperidin-4-ylcarbamoyl) phenylamino)oxazole-4-carboxamide; and 5-(4-((1-methylpiperidin-4-yl)carbamoyl)phenylamino)-2-(2,6-difluorophenyl) oxazole-4-carboxamide;

and salts thereof.

In another aspect, the invention provides a novel group of compounds within formula (0) of Embodiment 1.0. The novel compounds per se of the invention are as defined in Embodiments 1.38 to 1.96

1.38 A compound of the formula (2):

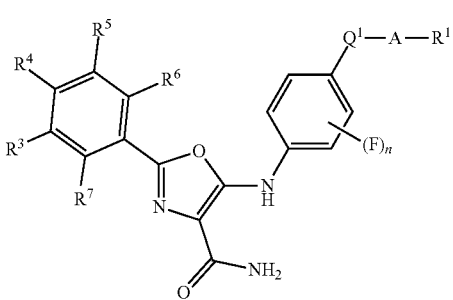 (2)

or a salt or stereoisomer thereof; wherein:

$R^7$ is selected from chlorine and fluorine;

$R^3$, $R^4$, $R^5$ and $R^6$ are each independently selected from hydrogen, fluorine and chlorine;

n is 0, 1 or 2;

$Q^1$ is selected from C(=O), S(=O) and $SO_2$;

A is absent or is $NR^2$;

$R^1$ is selected from:

hydrogen;

a $C_{1-6}$ non-aromatic hydrocarbon group optionally substituted with one or more substituents selected from hydroxyl, $C_{1-2}$ alkoxy, amino, mono-$C_{1-4}$ alkylamino, di-$C_{1-4}$ alkylamino, 3- to 7-membered non-aromatic carbocyclic and heterocyclic rings containing one or two heteroatom ring members selected from O, N and S, and bridged bicyclic heterocyclic rings of seven to nine ring members of which one or two are nitrogen atoms, the carbocylic and heterocyclic rings and bridged bicyclic heterocyclic rings being optionally substituted with one or more hydroxy, $C_{1-4}$ alkyl, $C_{1-4}$ alkoxy, $C_{1-4}$ alkanoyl, $C_{1-4}$ alkanoyloxy, $C_{1-4}$ alkoxycarbonyl or hydroxyl-$C_{1-3}$ alkyl groups; and 3- to 7-membered non-aromatic carbocyclic and heterocyclic rings containing one or two heteroatom ring members selected from O, N and S, and bridged bicyclic heterocyclic rings of seven to nine ring members of which one or two are nitrogen atoms, the carbocyclic and heterocyclic rings and bridged bicyclic heterocyclic rings being optionally substituted with one or more hydroxy, $C_{1-4}$ alkyl, $C_{1-4}$ alkoxy, $C_{1-4}$ alkanoyl, $C_{1-4}$ alkanoyloxy, $C_{1-4}$ alkoxycarbonyl, amino-$C_{1-3}$alkyl, mono-$C_{1-2}$ alkylamino-$C_{1-3}$ alkyl, di-$C_{1-2}$ alkylamino-$C_{1-3}$ alkyl or hydroxyl-$C_{1-3}$ alkyl groups;

$R^2$ is selected from hydrogen and $C_{1-4}$ alkyl; or $NR^1R^2$ forms a 4- to 7-membered non-aromatic nitrogen-containing heterocyclic ring optionally containing a second heteroatom ring member selected from nitrogen and oxygen, the heterocyclic ring being optionally substituted with one or more hydroxy, $C_{1-4}$ alkyl, $C_{1-4}$ alkanoyl, $C_{1-4}$ alkanoyloxy, $C_{1-4}$ alkoxy, $C_{1-4}$ alkoxycarbonyl amino-$C_{1-3}$alkyl, mono-$C_{1-2}$ alkylamino-$C_{1-3}$ alkyl, di-$C_{1-2}$ alkylamino-$C_{1-3}$ alkyl or hydroxy-$C_{1-3}$ alkyl groups; with the provisos that:

(i) more than two of $R^3$ to $R^6$ are other than hydrogen; and
(ii) when $R^7$ and $R^6$ are both fluorine, then one of $R^3$ to $R^5$ is chlorine or fluorine and/or $R^1$-A-$Q^1$ is selected from ethylsulfonyl and isopropylsulfonyl.

1.38A A compound according to Embodiment 1.38 provided that when $R^7$ and $R^6$ are both fluorine, then one of $R^3$ to $R^5$ is chlorine or fluorine.

1.39 A compound according to Embodiment 1.38 or Embodiment 1.38A wherein $R^7$ is chlorine.

1.40 A compound according to Embodiment 1.39 wherein $R^7$ is chlorine and $R^6$ is fluorine.

1.41 A compound according to Embodiment 1.39 wherein $R^7$ and $R^6$ are both chlorine.

1.42 A compound according to any one of Embodiments 1.38 to 1.41 wherein at least one of $R^3$ and $R^5$ is hydrogen.

1.43 A compound according to Embodiment 1.42 wherein both of $R^3$ and $R^5$ are hydrogen.

1.44 A compound according to any one of Embodiments 1.38 to 1.43 wherein $R^4$ is hydrogen.

1.45 A compound according to any one of Embodiments 1.38 to 1.43 wherein $R^4$ is fluorine.

1.46 A compound according to any one of Embodiments 1.38 to 1.43 wherein $R^4$ is chlorine.

1.47 A compound according to any one of Embodiments 1.38 to 1.46 wherein $Q^1$ is C(=O).

1.48 A compound according to any one of Embodiments 1.38 to 1.46 wherein $Q^1$ is S(=O).

1.49 A compound according to any one of Embodiments 1.38 to 1.46 wherein $Q^1$ is $SO_2$.

1.50 A compound according to any one of Embodiments 1.38 to 1.49 wherein A is absent (i.e. the moieties $R^1$ and $Q^1$ are directly joined together)

1.51 A compound according to Embodiment 1.50 wherein A is absent and $Q^1$ is $SO_2$.

1.52 A compound according to any one of Embodiments 1.38 to 1.49 wherein A is $NR^2$.

1.53 A compound according to any one of Embodiments 1.38 to 1.52 wherein:

$R^1$ is selected from:

hydrogen;

a $C_{1-6}$ saturated hydrocarbon group optionally substituted with one or more substituents selected from hydroxy, $C_{1-2}$ alkoxy, amino, mono-$C_{1-4}$ alkylamino, di-$C_{1-4}$ alkylamino, 3- to 6-membered saturated carbocyclic rings and 4 to 7 membered heterocyclic rings containing one or two heteroatom ring members selected from O, N and S, and bridged bicyclic heterocyclic rings of seven to nine ring members of which one or two are nitrogen atoms, the carbocyclic and heterocyclic rings and bridged bicyclic heterocyclic rings being optionally substituted with one or more hydroxy, $C_{1-4}$ alkyl, $C_{1-4}$ alkoxy, $C_{1-4}$ alkanoyl, $C_{1-4}$ alkanoyloxy, $C_{1-4}$ alkoxycarbonyl, amino-$C_{1-3}$ alkyl, mono-$C_{1-2}$ alkylamino-$C_{1-3}$ alkyl, di-$C_{1-2}$ alkylamino-$C_{1-3}$ alkyl or hydroxy-$C_{1-3}$ alkyl groups; and 3- to 6-membered saturated carbocyclic rings and 4 to 7 membered heterocyclic rings containing one or two heteroatom ring members selected from O, N and S, and bridged bicyclic heterocyclic rings of seven to nine ring members of which one or two are nitrogen atoms, the carbocyclic and heterocyclic rings and bridged bicyclic heterocyclic rings being optionally substituted with one or more hydroxy, $C_{1-4}$ alkyl, $C_{1-4}$ alkoxy, $C_{1-4}$ alkanoyl, $C_{1-4}$ alkanoyloxy, $C_{1-4}$ alkoxycarbonyl, amino-$C_{1-3}$ alkyl, mono-$C_{1-2}$ alkylamino-$C_{1-3}$ alkyl, di-$C_{1-2}$ alkylamino-$C_{1-3}$ alkyl or hydroxy-$C_{1-3}$ alkyl groups;

$R^2$, when present, is selected from hydrogen and $C_{1-4}$ alkyl; or $NR^1R^2$ forms a 4- to 7-membered saturated nitrogen-containing heterocyclic ring optionally containing a second heteroatom ring member selected from nitrogen and oxygen, the heterocyclic ring being optionally substituted with one or more hydroxy, $C_{1-4}$ alkyl, $C_{1-4}$ alkanoyl, $C_{1-4}$ alkanoyloxy, $C_{1-4}$ alkoxy, $C_{1-4}$ alkoxycarbonyl or hydroxy-$C_{1-3}$ alkyl groups.

1.54 A compound according to Embodiment 1.53 wherein:

$R^1$ is selected from:

hydrogen;

a $C_{1-4}$ alkyl group optionally substituted with one or more substituents selected from hydroxyl, $C_{1-3}$ alkoxy, amino, mono-$C_{1-3}$ alkylamino, di-$C_{1-3}$ alkylamino, 3- to 5-membered saturated carbocyclic rings and 4- to 6-membered heterocyclic rings containing one or two heteroatom ring members selected from O, N and S, the carbocyclic and heterocyclic rings being optionally substituted with one or more hydroxy, $C_{1-3}$ alkyl, $C_{1-3}$ alkoxy, $C_{1-3}$ alkanoyl, $C_{1-3}$ alkanoyloxy, $C_{1-3}$ alkoxycarbonyl, or hydroxy-$C_{1-3}$ alkyl groups; and 3- to 5-membered saturated carbocyclic rings and 4 to 6 membered non-aromatic heterocyclic rings containing one or two heteroatom ring members selected from O, N and S, the carbocyclic and heterocyclic rings being optionally substituted with one or more hydroxy, $C_{1-3}$ alkyl, $C_{1-3}$ alkoxy, $C_{1-3}$ alkanoyl, $C_{1-3}$ alkanoyloxy, $C_{1-4}$ alkoxycarbonyl or hydroxy-$C_{1-3}$ alkyl groups;

$R^2$, when present, is selected from hydrogen and $C_{1-2}$ alkyl; or $NR^1R^2$ forms a 4- to 7-membered saturated nitrogen-containing heterocyclic ring optionally containing a second heteroatom ring member selected from nitrogen and oxygen, the heterocyclic ring being optionally substituted with one or more hydroxy, $C_{1-3}$ alkyl, $C_{1-3}$ alkanoyl, $C_{1-3}$ alkanoyloxy, $C_{1-3}$ alkoxy, $C_{1-4}$ alkoxycarbonyl or hydroxy-$C_{1-3}$ alkyl groups.

1.55 A compound according to Embodiment 1.54 wherein:

$R^1$ is selected from:

hydrogen;

a $C_{1-4}$ alkyl group optionally substituted with one or more substituents selected from hydroxy, amino, mono-$C_{1-3}$ alkylamino and di-$C_{1-3}$ alkylamino; and 5 to 6-membered non-aromatic heterocyclic rings containing a nitrogen ring member and optionally a second ring member selected from N and O, the heterocyclic rings being optionally substituted with one or more $C_{1-3}$ alkyl or hydroxy-$C_{1-3}$ alkyl groups;

$R^2$, when present, is selected from hydrogen and $C_{1-2}$ alkyl; or $NR^1R^2$ forms a 5 to 6-membered heterocyclic ring containing a nitrogen ring member and optionally a second ring member selected from N and O, the heterocyclic rings being optionally substituted with one or more $C_{1-3}$ alkyl or hydroxy-$C_{1-3}$ alkyl groups.

1.56 A compound according to Embodiment 1.55 wherein:
$R^1$ is selected from:
hydrogen;
a $C_{1-4}$ alkyl group optionally substituted with one or more substituents selected from hydroxy, amino and mono-$C_{1-3}$ alkylamino; and
5 to 6-membered non-aromatic heterocyclic rings selected from pyrrolidine, piperidine, piperazine and morpholine, the heterocyclic rings being optionally substituted with one or more $C_{1-3}$ alkyl or hydroxy-$C_{1-3}$ alkyl groups;
$R^2$, when present, is selected from hydrogen and $C_{1-2}$ alkyl; or
$NR^1R^2$ forms a 5 to 6-membered heterocyclic ring selected from pyrrolidine, piperidine, piperazine and morpholine, the heterocyclic ring being optionally substituted with one or more $C_{1-3}$ alkyl or hydroxy-$C_{1-3}$ alkyl groups.

1.57 A compound according to Embodiment 1.56 wherein:
$R^1$ is selected from:
hydrogen;
a $C_{1-3}$ alkyl group optionally substituted with one or more substituents selected from hydroxy, amino and methylamino; and
5 to 6-membered heterocyclic rings selected from pyrrolidine, piperidine, piperazine and morpholine, the heterocyclic rings being optionally substituted with one or more $C_{1-3}$ alkyl or hydroxy-$C_{1-3}$ alkyl groups;
$R^2$, when present, is selected from hydrogen and $C_{1-2}$ alkyl; or
$NR^1R^2$ forms a 5 to 6-membered heterocyclic ring selected from pyrrolidine, piperidine, piperazine and morpholine, the heterocyclic ring being optionally substituted with one or more $C_{1-3}$ alkyl or hydroxy-$C_{1-3}$ alkyl groups.

1.58 A compound according to Embodiment 1.57 wherein:
$R^1$ is selected from:
hydrogen;
a $C_{1-3}$ alkyl group optionally substituted with one or more substituents selected from hydroxy, amino and methylamino; and
5 to 6-membered heterocyclic rings selected from pyrrolidine and piperidine, the heterocyclic rings being optionally substituted with a methyl group;
$R^2$, when present, is selected from hydrogen and methyl; or
$NR^1R^2$ forms a 5 to 6-membered heterocyclic ring selected from pyrrolidine and morpholine, the heterocyclic ring being optionally substituted with a hydroxymethyl group.

1.59 A compound according to any one of Embodiments 1.38 to 1.52 wherein $R^1$ is selected from:
hydrogen; and
a $C_{1-6}$ non-aromatic hydrocarbon group optionally substituted with one or more substituents selected from hydroxyl, $C_{1-2}$ alkoxy, amino, mono-$C_{1-4}$ alkylamino, di-$C_{1-4}$ alkylamino, 3- to 7-membered non-aromatic carbocyclic and heterocyclic rings containing one or two heteroatom ring members selected from O, N and S, and bridged bicyclic heterocyclic rings of seven to nine ring members of which one or two are nitrogen atoms, the carbocylic and heterocyclic rings and bridged bicyclic heterocyclic rings being optionally substituted with one or more hydroxy, $C_{1-4}$ alkyl, $C_{1-4}$ alkoxy, $C_{1-4}$ alkanoyl, $C_{1-4}$ alkanoyloxy, $C_{1-4}$ alkoxycarbonyl or hydroxyl-$C_{1-3}$ alkyl groups.

1.60 A compound according to any one of Embodiments 1.38 to 1.52 wherein $R^1$ is selected from:
hydrogen; and
a $C_{1-4}$ alkyl group optionally substituted with one or more substituents selected from hydroxyl, $C_{1-3}$ alkoxy, amino, mono-$C_{1-3}$ alkylamino, di-$C_{1-3}$ alkylamino, 3- to 5-membered saturated carbocyclic rings and 4- to 6-membered heterocyclic rings containing one or two heteroatom ring members selected from O, N and S, the carbocylic and heterocyclic rings being optionally substituted with one or more hydroxy, $C_{1-3}$ alkyl, $C_{1-3}$ alkoxy, $C_{1-3}$ alkanoyl, $C_{1-3}$ alkanoyloxy, $C_{1-3}$ alkoxycarbonyl, or hydroxy-$C_{1-3}$ alkyl groups.

1.61 A compound according to any one of Embodiments 1.38 to 1.52 wherein $R^1$ is selected from:
hydrogen; and
a $C_{1-4}$ alkyl group optionally substituted with one or more substituents selected from hydroxy, amino, mono-$C_{1-3}$ alkylamino and di-$C_{1-3}$ alkylamino.

1.62 A compound according to any one of Embodiments 1.38 to 1.52 wherein $R^1$ is selected from:
hydrogen; and
a $C_{1-4}$ alkyl group optionally substituted with one or more substituents selected from hydroxy, amino and mono-$C_{1-3}$ alkylamino.

1.63 A compound according to any one of Embodiments 1.38 to 1.52 wherein $R^1$ is selected from:
hydrogen; and
a $C_{1-3}$ alkyl group optionally substituted with one or more substituents selected from hydroxy, amino and methylamino.

1.64 A compound according to Embodiment 1.63 wherein $R^1$ is a $C_{1-3}$ alkyl group.

1.65 A compound according to Embodiment 1.64 wherein $R^1$ is selected from methyl, ethyl and isopropyl.

1.66 A compound according to Embodiment 1.65 wherein $R^1$ is methyl.

1.67 A compound according to Embodiment 1.65 wherein $R^1$ is ethyl.

1.68 A compound according to Embodiment 1.65 wherein $R^1$ is isopropyl.

1.69 A compound according to Embodiment 1.63 wherein $R^1$ is a $C_{1-3}$ alkyl group optionally substituted with one or more substituents selected from hydroxy, amino and methylamino.

1.70 A compound according to Embodiment 1.69 wherein $R^1$ is a $C_{2-3}$ alkyl group substituted with one or more substituents selected from hydroxy, amino and methylamino.

1.71 A compound according to Embodiment 1.70 wherein $R^1$ is selected from 3-aminopropyl, 3-methylaminopropyl, 2-methylaminoethyl, 3-hydroxypropyl and 2-hydroxyethyl.

1.73 A compound according to Embodiment 1.63 wherein $R^1$ is hydrogen.

1.74 A compound according to any one of Embodiments 1.38 to 1.52 wherein $R^1$ is selected from 3- to 6-membered saturated carbocyclic rings and 4 to 7 membered heterocyclic rings containing one or two heteroatom ring members selected from O, N and S, and bridged bicyclic heterocyclic rings of seven to nine ring members of which one or two are nitrogen atoms, the carbocylic and heterocyclic rings and bridged bicyclic heterocyclic rings being optionally substituted with one or more hydroxy, $C_{1-4}$ alkyl, $C_{1-4}$ alkoxy, $C_{1-4}$ alkanoyl, $C_{1-4}$ alkanoyloxy, $C_{1-4}$ alkoxycarbonyl, amino-$C_{1-3}$ alkyl, mono-$C_{1-2}$ alkylamino-$C_{1-3}$ alkyl, di-$C_{1-2}$ alkylamino-$C_{1-3}$ alkyl or hydroxy-$C_{1-3}$ alkyl groups.

1.75 A compound according to any one of Embodiments 1.38 to 1.52 wherein $R^1$ is selected from 3- to 5-membered saturated carbocyclic rings and 4 to 6 membered non-aromatic heterocyclic rings containing one or two heteroatom ring members selected from O, N and S, the carbocyclic and heterocyclic rings being optionally substituted with one or more hydroxy, $C_{1-3}$ alkyl, $C_{1-3}$ alkoxy, $C_{1-3}$ alkanoyl, $C_{1-3}$ alkanoyloxy, $C_{1-4}$ alkoxycarbonyl or hydroxy-$C_{1-3}$ alkyl groups.

1.76 A compound according to any one of Embodiments 1.38 to 1.52 wherein $R^1$ is selected from 5 to 6-membered non-aromatic heterocyclic rings containing a nitrogen ring member and optionally a second ring member selected from N and O, the heterocyclic rings being optionally substituted with one or more $C_{1-3}$ alkyl or hydroxy-$C_{1-3}$ alkyl groups.

1.77 A compound according to any one of Embodiments 1.38 to 1.52 wherein $R^1$ is a 5- or 6-membered non-aromatic heterocyclic ring selected from pyrrolidine, piperidine, piperazine and morpholine, the heterocyclic ring being optionally substituted with one or more $C_{1-3}$ alkyl or hydroxy-$C_{1-3}$ alkyl groups.

1.78 A compound according to Embodiment 1.57 wherein $R^1$ is a 5 to 6-membered heterocyclic ring selected from pyrrolidine and piperidine, the heterocyclic ring being optionally substituted with a methyl group.

1.79 A compound according to any one of Embodiments 1.38 to 1.49 wherein A is $NR^2$ and $NR^1R^2$ forms a 4- to 7-membered saturated nitrogen-containing heterocyclic ring optionally containing a second heteroatom ring member selected from nitrogen and oxygen, the heterocyclic ring being optionally substituted with one or more hydroxy, $C_{1-4}$ alkyl, $C_{1-4}$ alkanoyl, $C_{1-4}$ alkanoyloxy, $C_{1-4}$ alkoxy, $C_{1-4}$ alkoxycarbonyl or hydroxy-$C_{1-3}$ alkyl groups.

1.80 A compound according to any one of Embodiments 1.38 to 1.49 wherein A is $NR^2$ and $NR^1R^2$ forms a 4- to 7-membered saturated nitrogen-containing heterocyclic ring optionally containing a second heteroatom ring member selected from nitrogen and oxygen, the heterocyclic ring being optionally substituted with one or more hydroxy, $C_{1-3}$ alkyl, $C_{1-3}$ alkanoyl, $C_{1-3}$ alkanoyloxy, $C_{1-3}$ alkoxy, $C_{1-4}$ alkoxycarbonyl or hydroxy-$C_{1-3}$ alkyl groups.

1.81 A compound according to any one of Embodiments 1.38 to 1.49 wherein A is $NR^2$ and $NR^1R^2$ forms a 5 to 6-membered heterocyclic ring containing a nitrogen ring member and optionally a second ring member selected from N and O, the heterocyclic rings being optionally substituted with one or more $C_{1-3}$ alkyl or hydroxy-$C_{1-3}$ alkyl groups.

1.82 A compound according to any one of Embodiments 1.38 to 1.49 wherein A is $NR^2$ and $NR^1R^2$ forms a 5 to 6-membered heterocyclic ring selected from pyrrolidine, piperidine, piperazine and morpholine, the heterocyclic ring being optionally substituted with one or more $C_{1-3}$ alkyl or hydroxy-$C_{1-3}$ alkyl groups.

1.83 A compound according to any one of Embodiments 1.38 to 1.49 wherein A is $NR^2$ and $NR^1R^2$ forms a 5 to 6-membered heterocyclic ring selected from pyrrolidine and morpholine, the heterocyclic ring being optionally substituted with a hydroxymethyl group.

1.84 A compound according to any one of Embodiments 1.38 to 1.49 and 1.52 to 1.78 wherein $R^2$ is selected from hydrogen and methyl.

1.85 A compound according to any one of Embodiments 1.38 to 1.49 and 1.52 to 1.78 wherein $R^2$ is hydrogen.

1.86 A compound according to any one of Embodiments 1.38 to 1.49 and 1.52 to 1.78 wherein $R^2$ is methyl.

1.87 A compound according to any one of Embodiments 1.38 to 1.46 wherein $Q^1$-A-$R^1$ is selected from groups AA to AT in the table below:

| | |
|---|---|
| 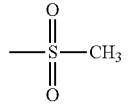 | AA |
| 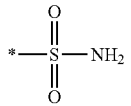 | AB |
| 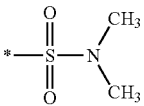 | AC |
| 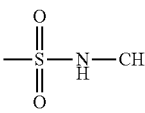 | AD |
| 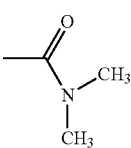 | AE |
| 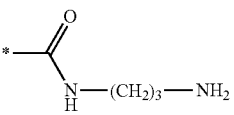 | AF |
| 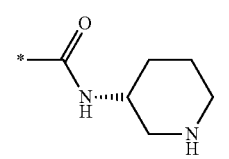 | AG |
| 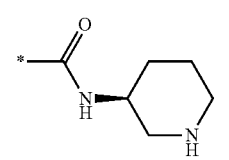 [SMILES: *C(=O)N[C@H]1CCCNC1] | AH |
| 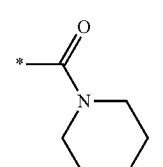 | AI |
| 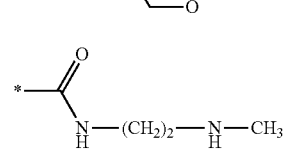 | AJ |
| 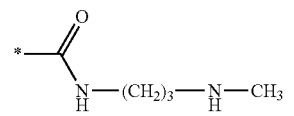 | AK |

-continued

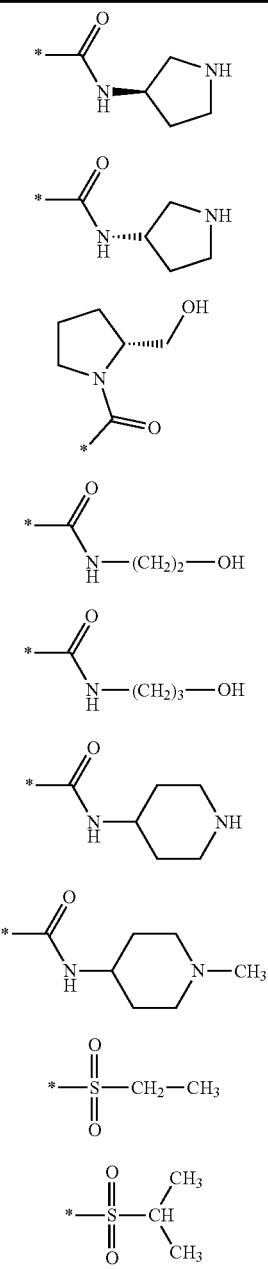

wherein the point of attachment to the phenyl group is indicated by the asterisk.

1.88 A compound according to Embodiment 1.87 wherein $Q^1$-A-$R^1$ is selected from groups AA, AG, AH, AI, AR, AS and AT.

1.89 A compound according to Embodiment 1.88 wherein $Q^1$-A-$R^1$ is selected from groups AA, AS and AT.

1.90 A compound according to Embodiment 1.89 wherein $Q^1$-A-$R^1$ is a group AA.

1.91 A compound according to Embodiment 1.88 wherein $Q^1$-A-$R^1$ is selected from groups AG, AH, AI and AR.

1.92 A compound according to any one of Embodiments 1.38 to 1.91 wherein n is selected from 0 and 1.

1.93 A compound according to Embodiment 1.92 wherein n is 0.

1.94 A compound according to Embodiment 1.92 wherein n is 1.

1.95 A compound according to Embodiment 1.94 wherein the fluorine atom is attached to the benzene ring at a position ortho with respect to the moiety $Q^1$.

1.96 A compound according to Embodiment 1.38 wherein the compound of formula (2) is selected from:

2-(2,6-dichloro-phenyl)-5-(4-methanesulfonyl-phenylamino)-oxazole-4-carboxylic acid amide;

2-(2-chloro-6-fluoro-phenyl)-5-(4-methanesulfonyl-phenylamino)-oxazole-4-carboxylic acid amide;

5-(4-methanesulfonyl-phenylamino)-2-(2,4,6-trifluoro-phenyl)-oxazole-4-carboxylic acid amide;

2-(2,5-difluoro-phenyl)-5-(4-methanesulfonyl-phenylamino)-oxazole-4-carboxylic acid amide;

(S) 2-(2-chloro-6-fluoro-phenyl)-5-[4-(piperidin-3-ylcarbamoyl)-phenylamino]-oxazole-4-carboxylic acid amide;

(R) 2-(2-chloro-6-fluoro-phenyl)-5-[4-(piperidin-3-ylcarbamoyl)-phenylamino]-oxazole-4-carboxylic acid amide;

2-(2-chloro-6-fluoro-phenyl)-5-[4-(morpholine-4-carbonyl)-phenylamino]-oxazole-4-carboxylic acid amide;

2-(2-chloro-6-fluoro-phenyl)-5-[4-(1-methyl-piperidin-4-ylcarbamoyl)-phenylamino]-oxazole-4-carboxylic acid amide;

(S) 2-(2,6-dichloro-phenyl)-5-[4-(piperidin-3-ylcarbamoyl)-phenylamino]-oxazole-4-carboxylic acid amide;

(R) 2-(2,6-dichloro-phenyl)-5-[4-(piperidin-3-ylcarbamoyl)-phenylamino]-oxazole-4-carboxylic acid amide;

2-(2,6-dichloro-phenyl)-5-[4-(morpholine-4-carbonyl)-phenylamino]-oxazole-4-carboxylic acid amide;

2-(2,6-dichloro-phenyl)-5-[4-(1-methyl-piperidin-4-ylcarbamoyl)-phenylamino]-oxazole-4-carboxylic acid amide;

2-(2,6-difluoro-phenyl)-5-(4-ethanesulfonyl-phenylamino)-oxazole-4-carboxylic acid amide;

2-(2,6-difluoro-phenyl)-5-(4-methanesulfonyl-phenylamino)-oxazole-4-carboxylic acid amide; and 2-(2,6-difluoro-phenyl)-5-[4-propane-2-sulfonyl)-henylamino]-oxazole-4-carboxylic acid amide;

and salts and stereoisomers thereof.

1.97 A method according to any one of Embodiments 1.0 to 1.37 or a compound according to any one of Embodiments 1.38 to 1.96 wherein the compound of formula (0), (1) or (2) is in the form of a salt.

1.98 A method or a compound according to Embodiment 1.97 wherein the salt is an acid addition salt.

1.99 A method or compound according to Embodiment 1.97 or Embodiment 1.98 wherein the acid addition salt is a pharmaceutically acceptable salt.

1.100 A method according to any one of Embodiments 1.0 to 1.37 or a compound according to any one of Embodiments 1.38 to 1.96 wherein the compound of formula (0), (1) or (2) is in the form of a free base.

Definitions

References to formula (1) below include formulae (0) and (2) as well as formula (1) unless the context indicates otherwise.

The term "non-aromatic hydrocarbon group", as in "$C_{1-6}$ non-aromatic hydrocarbon group", as used herein refers to a structural group consisting of carbon and hydrogen and which does not have aromatic character.

Unless indicated otherwise, the non-aromatic hydrocarbon group can be acyclic or cyclic and can be saturated or unsaturated. Thus the term covers alkyl, alkenyl, alkynyl, cycloalkyl and cycloalkenyl groups and combinations thereof.

Where specified, non-aromatic hydrocarbon groups can be substituted; i.e. a hydrogen atom may be replaced by another atom or functional group.

References to "non-aromatic carbocyclic and heterocyclic rings" as used herein refer to both saturated and unsaturated ring systems provided that any such unsaturated ring systems do not have aromatic character, The term "bridged bicyclic heterocyclic rings" as used herein refers to non-aromatic heterocyclic ring systems in which two rings share more than two atoms, see for example Advanced Organic Chemistry, by Jerry March, 4th Edition, Wiley Interscience, pages 131-133, 1992. The bridged bicyclic ring systems can be, for example, [3.2.1] bicyclic ring systems such as an 8-aza-bicyclo[3.2.1]octane-3-yl group, or [2.2.2] biyclic ring systems such as a quinuclidin-3-yl group.

Salts

The compounds of formulae (0), (1) and (2) may be presented in the form of salts.

The salts (as defined in Embodiments 1.97 to 1.99) are typically acid addition salts.

The salts can be synthesized from the parent compound by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free base form of the compound with the acid in water or in an organic solvent, or in a mixture of the two; generally, nonaqueous media such as ether, ethyl acetate, ethanol, isopropanol, or acetonitrile are used.

Acid addition salts (as defined in Embodiment 1.98) may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, (+)-L-lactic, (±)-DL-lactic, lactobionic, maleic, malic, (−)-L-malic, malonic, (±)-DL-mandelic, methanesulphonic, naphthalene-2-sulphonic, naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, (+)-L-tartaric, thiocyanic, p-toluenesulphonic, undecylenic and valeric acids, as well as acylated amino acids and cation exchange resins.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Isotopes

The compounds of the invention as defined in any one of Embodiments 1.0 to 1.100 may contain one or more isotopic substitutions, and a reference to a particular element includes within its scope all isotopes of the element. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$.

In an analogous manner, a reference to a particular functional group also includes within its scope isotopic variations, unless the context indicates otherwise.

For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group).

The isotopes may be radioactive or non-radioactive. In one embodiment of the invention (Embodiment 1.101), the compound of any one of Embodiments 1.0 to 1.100 contains no radioactive isotopes. Such compounds are preferred for therapeutic use. In another embodiment (Embodiment 1.102), however, the compound of any one of Embodiments 1.0 to 1.100 may contain one or more radioisotopes. Compounds containing such radioisotopes may be useful in a diagnostic context.

Solvates

Compounds of the formulae (0), (1) or (2) as defined in any one of Embodiments 1.0 to 1.102 may form solvates.

Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallizing the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates.

Particularly preferred solvates are hydrates, and examples of hydrates include hemihydrates, monohydrates and dihydrates.

Accordingly, in further embodiments 1.103 and 1.104, the invention provides:

1.103 A method or compound according to any one of Embodiments 1.0 to 1.102 wherein the compound of formula (0), (1) or (2) is in the form of a solvate.

1.104 A method or compound according to Embodiment 1.103 wherein the solvate is a hydrate.

For a more detailed discussion of solvates and the methods used to make and characterise them, see Bryn et al., Solid-State Chemistry of Drugs, Second Edition, published by SSCI, Inc. of West Lafayette, Ind., USA, 1999, ISBN 0-967-06710-3.

Alternatively, rather than existing as a hydrate, the compound of the invention may be anhydrous. Therefore, in another embodiment (Embodiment 1.105), the compound of formula (1) as defined in any one of Embodiments 1.0 to 1.102 is in an anhydrous form.

Inhibition of TYK2 Kinase and Therapeutic Uses Arising Therefrom

In Embodiments 1.0 to 1.37, there is provided a method of inhibiting a TYK2 kinase, which method comprises bringing into contact with the TYK2 kinase an effective TYK2 kinase-inhibiting amount of a compound having the formula (0) or formula (1).

The inhibition of the TYK2 kinase may take place either in vitro or in vivo.

Accordingly, the invention provides:

2.1 A method according to any one of Embodiments 1.0 to 1.37 and 1.97 to 1.105 wherein the inhibition of the TYK2 kinase takes place in vitro.

2.2 A method according to any one of Embodiments 1.1 to 1.37 and 1.97 to 1.105 wherein the inhibition of the TYK2 kinase takes place in vivo.

The novel compounds of Embodiments 1.38 to 1.105 can also be used for inhibiting TYK2 kinase. Accordingly, the invention further provides:

2.3 A method of inhibiting a TYK2 kinase, which method comprises bringing into contact with the TYK2 kinase an effective TYK2 kinase-inhibiting amount of a compound having the formula (2) or a salt or stereoisomer thereof as defined in any one of Embodiments 1.38 to 1.105.

2.4 A method according to Embodiment 2.3 wherein the inhibition of the TYK2 kinase takes place in vitro.

2.5 A method according to Embodiment 2.4 wherein the inhibition of the TYK2 kinase takes place in vivo.

2.6 A compound of the formula (0), (1) or (2) as defined in any one of Embodiments 1.0 to 1.105 for use as an inhibitor of TYK2 kinase.

2.7 A compound of the formula (2) as defined in any one of Embodiments 1.38 to 1.105 for use in medicine.

The inhibition of TYK2 kinase preferably takes place in vivo as part of a therapeutic treatment of a disease or condition in which TYK2 kinase is implicated.

The method of the invention is particularly applicable in the context of treating a disease or condition selected from an inflammatory disease or condition, an immunological disease or condition, an allergic disease or disorder, a transplant rejection and Graft-versus host disease. The method is also applicable in the context of treating sepsis and septic shock.

Accordingly, in further aspects, the invention provides:

2.8 A method of treating a disease or condition in a subject in need thereof, wherein the disease is selected from an inflammatory disease or condition, an immunological disease or condition, an allergic disease or disorder, a transplant rejection and Graft-versus host disease, or a disease or condition selected from sepsis and septic shock, wherein the disease or condition is susceptible to TYK2 inhibition, which method comprises administering to the subject an effective TYK2 inhibiting amount of a compound of the formula (0), (1) or (2) or a salt thereof as defined in any one of Embodiments 1.0 to 1.105.

2.9 A compound of the formula (0), (1) or (2), or a salt thereof, as defined in any one of Embodiments 1.0 to 1.105 for use in the treatment of an inflammatory disease or condition, an immunological disease or condition, an allergic disease or disorder, a transplant rejection and Graft-versus host disease; or for use in the treatment of sepsis or septic shock, wherein the disease or condition is susceptible to TYK2 inhibition.

2.10 The use of a compound of the formula (0), (1) or (2), or a salt thereof, as defined in any one of Embodiments 1.0 to 1.105 for the manufacture of a medicament for the treatment of an inflammatory disease or condition, an immunological disease or condition, an allergic disease or disorder, a transplant rejection and Graft-versus host disease; or for use in the treatment of sepsis or septic shock, wherein the disease or condition is susceptible to TYK2 inhibition.

Autoimmune Diseases

The TYK2 inhibitory activity of the compounds of formulae (0), (1) and (2) can be made use of in treating autoimmune diseases. Thus, in further aspects, the invention provides:

2.11 A method of treating an autoimmune disease in a subject in need thereof, which method comprises administering to the subject an effective TYK2 inhibiting amount of a compound of the formula (0), (1) or (2), as defined in any one of Embodiments 1.0 to 1.105, so as to inhibit TYK2 kinase in the subject and thereby block or reduce the extent of an inflammatory process associated with the autoimmune disease.

2.12 A compound of the formula (0), (1) or (2), as defined in any one of Embodiments 1.0 to 1.105, for use in a method of treating an autoimmune disease in a subject in need thereof, which method comprises administering to the subject an effective TYK2 inhibiting amount of the said compound, so as to inhibit TYK2 kinase in the subject and thereby block or reduce the extent of an inflammatory process associated with the autoimmune disease.

2.13 The use of a compound of the formula (0), (1) or (2), as defined in any one of Embodiments 1.0 to 1.105, for the manufacture of a medicament for treating an autoimmune disease in a subject in need thereof by administering to the subject an effective TYK2 inhibiting amount of the said compound, so as to inhibit TYK2 kinase in the subject and thereby block or reduce the extent of an inflammatory process associated with the autoimmune disease.

2.14 A method, compound for use or use according to any one of Embodiments 2.11 to 2.13 wherein the autoimmune disease is multiple sclerosis.

Experimental autoimmune encephalomyelitis (EAE) and Theiler's murine encephalitis virus-induced demyelinating disease (TMEV-IDD) are two clinically relevant murine models of multiple sclerosis (MS) (see (i) Raine CS: *Biology of disease. The analysis of autoimmune demyelination: its impact upon multiple sclerosis. Lab Invest* 1984, 50:608-635; (ii) Steinman L: *Assessment to the utility of animal models for MS and demyelinating disease in the design of rational therapy. Neuron* 1999, 24:511-514; and (iii) Kevin G. Fuller et al., *Mouse Models of Multiple Sclerosis: Experimental Autoimmune Encephalomyelitis and Theiler's Virus-Induced Demyelinating Disease, Autoimmunity: Methods and Protocols*, (Series: *Methods in Molecular Medicine*), Volume: 102, 2004, 339-361)

The usefulness of the compounds of formulae (0), (1) or (2) in treating multiple sclerosis can be demonstrated using either of the above models and in particular the experimental autoimmune encephalomyelitis (EAE) model described in the examples below.

The terms "treating" and "treatment" as used herein in the context of multiple sclerosis include any one or more of:
halting the progression of the disease;
slowing the progression of the disease;
modifying the progression of the disease;
providing symptomatic relief, e.g. by eliminating or reducing the severity of one or more symptoms;
extending periods of remission;
preventing relapses;
reducing the severity of relapses; and
preventing or slowing the progression from an initial period of relapsing-remitting MS to secondary progressive MS.

Symptoms of multiple sclerosis that may be eliminated or reduced in severity in accordance with the invention include any one or more symptoms, in any combination, selected from:
weakness and/or numbness in one or more extremities;
tingling of the extremities;
tight band-like sensations around the trunk or limbs;
tremor of one or more extremities;
dragging or poor control of one or both legs;
spastic or ataxic paraparesis;
paralysis of one or more extremities;
hyperactive tendon reflexes;
disappearance of abdominal reflexes;
Lhermitte's sign;
retrobulbar or optic neuritis;
unsteadiness in walking;
problems with balance,
increased muscle fatigue;
brain stem symptoms (diplopia, vertigo, vomiting);
disorders of micturition;
hemiplegia;
trigeminal neuralgia;
other pain syndromes;
nystagmus and ataxia;
cerebellar-type ataxia;
Charcot's triad; diplopia;
bilateral internuclear ophthalmoplegia;
myokymia or paralysis of facial muscles;
deafness;
tinnitus;
unformed auditory hallucinations (because of involvement of cochlear connections);
transient facial anesthesia or of trigeminal neuralgia;
urinary and/or faecal incontinence
bladder dysfunction euphoria;
depression;
fatigue;
dementia;
dull, aching pain in the lower back;
sharp, burning, poorly localized pains in a limb;
abrupt attacks of neurologic deficit;
dysarthria and ataxia;
paroxysmal pain and dysesthesia in a limb;
flashing lights;
paroxysmal itching;
tonic seizures;
changes in sensation;
visual problems;
muscle weakness;
difficulties with coordination and speech;
cognitive impairment;
overheating; and
impaired mobility and disability.

The compound may be used in a prophylactic sense during periods of remission in order to prevent or reduce the likelihood or severity of relapses or it may be used to treat patients who are suffering from a relapse. Preferably it is used in a prophylactic sense.

The compound of the formulae (0), (1) or (2) or a pharmaceutically acceptable salt thereof may be used as the sole therapeutic agent or it may be used in conjunction with other therapeutic agents such as steroids or interferons.

In one general embodiment of the invention, the compound of the formula (0), (1) or (2) or pharmaceutically acceptable salt thereof is used as the sole therapeutic agent.

Use in Treating Diseases and Conditions Other than Multiple Sclerosis

Whilst the TYK2 inhibitory activity of the compounds of formula (1) can be made use of in the treatment of autoimmune diseases, it can also be put to good use in the treatment of a range of other inflammatory diseases, as well as immunological and allergic diseases. Accordingly, the invention also provides:

2.15 A method of treating a disease or condition in a subject in need thereof, wherein the disease is other than an autoimmune disease and is selected from an inflammatory disease or condition, an immunological disease or condition, an allergic disease or disorder, a transplant rejection and Graft-versus host disease wherein the disease or condition is susceptible to TYK2 inhibition, which method comprises administering to the subject an effective TYK2 inhibiting amount of a compound of the formula (0), (1) or (2) or a salt thereof as defined in any one of Embodiments 1.0 to 1.105.

2.16 A method of treating a disease or condition in a subject in need thereof, wherein the disease is other than multiple sclerosis and is selected from an inflammatory disease or condition, an immunological disease or condition, an allergic disease or disorder, a transplant rejection and Graft-versus host disease wherein the disease or condition is susceptible to TYK2 inhibition, which method comprises administering to the subject an effective TYK2 inhibiting amount of a compound of the formula (0), (1) or (2) or a salt thereof as defined in any one of Embodiments 1.0 to 1.105.

2.17 A method of treating a disease or condition in a subject in need thereof, wherein the disease is any one or more diseases or conditions selected from:
(a) skin inflammation due to radiation exposure;
(b) asthma;
(c) allergic inflammation;
(d) chronic inflammation;
(e) an inflammatory ophthalmic disease;
(f) dry eye syndrome (DES, also known as keratoconjunctivitis sicca or dysfunctional tear syndrome);
(g) uveitis (e.g. chronic progressive or relapsing forms of non-infectious uveitis);
(h) insulin-dependent diabetes (Type I);
(i) Hashimoto's thyroiditis;
(j) Graves' disease;
(k) Cushing's disease;
(l) Addison's disease (which affect the adrenal glands)
(m) chronic active hepatitis (which affects the liver);
(n) polycystic ovary syndrome (PCOS);
(o) coeliac disease;
(p) psoriasis;
(q) inflammatory bowel disease (IBD);
(r) ankylosing spondylitis;
(s) rheumatoid arthritis;
(t) systemic lupus erythematosus;

(u) myasthenia gravis;

(v) transplant rejection (allograft transplant rejection); and (w) graft-versus-host disease (GVDH);

which method comprises administering to the subject an effective TYK2 inhibiting amount of a compound of the formula (0), (1) or (2) or a salt thereof as defined in any one of Embodiments 1.0 to 1.105.

2.18 A compound of the formula (0), (1) or (2) as defined in any one of Embodiments 1.0 to 1.105 for use in a method as defined in any one of Embodiments 2.15, 2.16 and 2.17.

2.19 The use of a compound of the formula (0), (1) or (2) as defined in any one of Embodiments 1.0 to 1.105 for the manufacture of a medicament for use in a method as defined in any one of Embodiments 2.15, 2.16 and 2.17.

In the context of the present invention, an autoimmune disease is a disease which is at least partially provoked by an immune reaction of the body against its own components, for example proteins, lipids or DNA. Examples of organ-specific autoimmune disorders are insulin-dependent diabetes (Type I) which affects the pancreas, Hashimoto's thyroiditis and Graves' disease which affect the thyroid gland, pernicious anemia which affects the stomach, Cushing's disease and Addison's disease which affect the adrenal glands, chronic active hepatitis which affects the liver; polycystic ovary syndrome (PCOS), celiac disease, psoriasis, inflammatory bowel disease (IBD) and ankylosing spondylitis. Examples of non-organ-specific autoimmune disorders are rheumatoid arthritis, multiple sclerosis, systemic lupus and myasthenia gravis. Type I diabetes ensues from the selective aggression of autoreactive T-cells against insulin secreting beta-cells of the islets of Langerhans.

Rheumatoid arthritis (RA) is a chronic progressive, debilitating inflammatory disease that affects approximately 1% of the world's population. RA is a symmetric polyarticular arthritis that primarily affects the small joints of the hands and feet. In addition to inflammation in the synovium, the joint lining, the aggressive front of tissue called pannus invades and destroys local articular structures (Firestein 2003, Nature 423:356-361).

Inflammatory bowel disease (IBD) is characterized by a chronic relapsing intestinal inflammation. IBD is subdivided into Crohn's disease and ulcerative colitis phenotypes. Crohn's disease involves most frequently the terminal ileum and colon, is transmural and discontinuous. In contrast, in ulcerative colitis, the inflammation is continuous and limited to rectal and colonic mucosal layers. In approximately 10% of cases confined to the rectum and colon, definitive classification of Crohn's disease or ulcerative colitis cannot be made and are designated 'indeterminate colitis'. Both diseases include extraintestinal inflammation of the skin, eyes, or joints. Neutrophil-induced injuries may be prevented by the use of neutrophil migration inhibitors (Asakura et al., 2007, World J. Gastroenterol. 13(15):2145-9).

Psoriasis is a chronic inflammatory dermatosis that affects approximately 2% of the population. It is characterized by red, scaly skin patches that are usually found on the scalp, elbows, and knees, and may be associated with severe arthritis. The lesions are caused by abnormal keratinocyte proliferation and infiltration of inflammatory cells into the dermis and epidermis (Schon et al, 2005, New Engl. J. Med. 352: 1899-1912). Systemic lupus erythematosus (SLE) is a chronic inflammatory disease generated by T cell-mediated B-cell activation, which results in glomerulonephritis and renal failure. Human SLE is characterized at early stages by the expansion of long-lasting autoreactive CD4+ memory cells (D'Cruz et al, 2007, Lancet 369(9561):587-596).

Transplant rejection (allograft transplant rejection) includes, without limitation, acute and chronic allograft rejection following for example transplantation of kidney, heart, liver, lung, bone marrow, skin and cornea. It is known that T cells play a central role in the specific immune response of allograft rejection. Hyperacute, acute and chronic organ transplant rejection may be treated. Hyperacute rejection occurs within minutes of transplantation. Acute rejection generally occurs within six to twelve months of the transplant. Hyperacute and acute rejections are typically reversible where treated with immunosuppressant agents. Chronic rejection, characterized by gradual loss of organ function, is an ongoing concern for transplant recipients because it can occur any time after transplantation.

Graft-versus-host disease (GVDH) is a major complication in allogeneic bone marrow transplantation (BMT). GVDH is caused by donor T cells that recognize and react to recipient differences in the histocompatibility complex system, resulting in significant morbidity and mortality.

Compounds of the formulae (0), (1) and (2) can also be used in the treatment of diseases or conditions characterized or caused (at least in part) by or associated with overexpression (elevated expression) of TYK2 kinase. One disease which has been shown to be associated with elevated levels of TYK2 is pulmonary sarcoidosis.

Pulmonary sarcoidosis is a relatively rare inflammatory disorder of unknown cause which typically develops in adults of 20 to 50 years of age. Pulmonary sarcoidosis is characterised by small lumps, or granulomas in the lungs, which generally heal and disappear on their own. However, for those granulomas that do not heal, the tissue can remain inflamed and become scarred, or fibrotic. Pulmonary sarcoidosis can develop into pulmonary fibrosis, which distorts the structure of the lungs and can interfere with breathing.

Therefore, in further aspects, the invention provides:

2.20 A method of treating a disease or condition in a subject in need thereof, wherein the disease is one which is characterized or caused (at least in part) by or associated with overexpression (elevated expression) of TYK2 kinase, which method comprises administering to the subject an effective TYK2 inhibiting amount of a compound of the formula (0), (1) or (2) or a salt thereof as defined in any one of Embodiments 1.0 to 1.105.

2.21 A method according to Embodiment 2.20 wherein the disease or condition is pulmonary sarcoidosis.

2.22 A compound of the formula (0), (1) or (2) or a salt thereof as defined in any one of Embodiments 1.0 to 1.105 for use in a method as defined in Embodiment 2.20 or 2.21.

2.23 The use of compound of the formula (0), (1) or (2) or a salt thereof as defined in any one of Embodiments 1.0 to 1.105 for the manufacture of a medicament for use in a method as defined in Embodiment 2.20 or 2.21.

Other Aspects

In further aspects (Embodiments 2.24 to 2.26), the invention provides:

2.24 A compound of the formula (0), (1) or (2) or a salt thereof as defined in any one of Embodiments 1.0 to 1.105 for use in inhibiting TYK2 kinase.

2.25 A compound of the formula (0), (1) or (2) or a salt thereof as defined in any one of Embodiments 1.0 to 1.105 for use in treating a disease or condition selected from an inflammatory disease or condition, an immunological disease or condition, an allergic disease or disorder, a transplant rejection and Graft-versus host disease, as defined herein.

2.26 The use of a compound of the formula (0), (1) or (2) or a salt thereof as defined in any one of Embodiments 1.0 to 1.105 for the manufacture of a medicament for treating a disease or condition selected from an inflammatory disease or condition, an immunological disease or condition, an allergic disease or disorder, a transplant rejection and Graft-versus-host disease, as defined herein.

The activity of the compounds of formulae (0), (1) and (2) as TYK2 inhibitors can be measured using the assay set forth in the examples below and the level of activity exhibited by a given compound can be defined in terms of the $IC_{50}$ value. Preferred compounds of the present invention are compounds having an $IC_{50}$ value of less than 0.03 μM.

An advantage of compounds of the formulae (0), (1) and (2) as defined herein is that they exhibit selectivity for TYK2 kinase compared to other kinases of the JAK family.

For example, the majority of the compounds of formulae (0), (1) and (2) exemplified herein have at least a tenfold selectivity for TYK2 compared to JAK2 and JAK3 and at least a fivefold selectivity for TYK2 versus JAK1.

Whilst selectivity for TYK2 is considered advantageous, it is envisaged that, in some circumstances, activity against other JAK kinases as well as TYK2 may be beneficial. Thus, for example, compounds of the formula (0), (1) or (2) as defined herein may have $IC_{50}$ values against TYK2 of less than 200 nanomolar (e.g. less than 50 nanomolar) and $IC_{50}$ values against JAK1, JAK2 and JAK3 of less than 500 nanomolar (e.g. less than 200 nanomolar), but wherein the activity against TYK2 is greater than the activity against any of JAK1, JAK2 and JAK3.

Methods for the Preparation of Compounds of Formulae (0), (1) and (2)

The compounds of formula (0), (1) and (2) can be prepared by the methods described in International patent application WO2008/139161 (Sareum): for example using the methods described in Examples Q-3, Q-14, Q-20, Q-21, Q-22, Q-25, Q-26, Q-27, Q-28, Q-29, Q-50, Q-51, Q-52 Q-53, Q-54, Q-55, Q-57, U-2, U-3, U-4, U-6, U-7, U-8, U-9, U-12, U-13, U-14, U-15, U-16, U-17, U-18, U-19, U-24, U-25, U-26 and U-27 and methods analogous thereto. Methods for the preparation of compounds of the formula (2) are also set out below in the Examples section.

Pharmaceutical Formulations

While it is possible for the active compound to be administered alone, it is preferable to present it as a pharmaceutical composition (e.g. formulation) comprising at least one active compound of the invention together with one or more pharmaceutically acceptable excipients such as carriers, adjuvants, diluents, fillers, buffers, stabilisers, preservatives, lubricants, or other materials well known to those skilled in the art, and optionally other therapeutic or prophylactic agents.

The term "pharmaceutically acceptable" as used herein refers to compounds, materials, compositions, and/or dosage forms which are, within the scope of sound medical judgment, suitable for use in contact with the tissues of a subject (e.g. human) without excessive toxicity, irritation, allergic response, or other problems or complication, commensurate with a reasonable benefit/risk ratio. Each excipient must also be "acceptable" in the sense of being compatible with the other ingredients of the formulation.

The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Pharmaceutical compositions containing compounds of the formulae (0), (1) and (2) can be formulated in accordance with known techniques, see for example, Remington's Pharmaceutical Sciences, Mack Publishing Company, Easton, Pa., USA.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable cross-linked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (e.g. tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively releasing the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Compositions for parenteral administration may be formulated for administration as discrete dosage units or may be formulated for administration by infusion.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the inventions will generally be presented in unit dosage form and, as such, will typically contain sufficient compound to provide a desired level of biological activity. For example, a formulation intended for oral administration may contain from 0.1 milligrams to 2 grams of active ingredient, more usually from 10 milligrams to 1 gram, for example, 50 milligrams to 500 milligrams.

The active compound will be administered to a patient in need thereof (for example a human or animal patient) in an amount sufficient to achieve the desired therapeutic effect.

Methods of Treatment

It is envisaged that the compounds of the formulae (0), (1) and (2) as defined in any one of Embodiments 1.0 to 1.105 will be useful in the prophylaxis or treatment of inflammatory diseases or conditions, immunological diseases or conditions, allergic diseases or disorders, transplant rejections and Graft-versus host disease. Examples of such disease states and conditions are set out above.

The compounds will typically be administered in amounts that are therapeutically or prophylactically useful and which generally are non-toxic. However, in certain situations (for example in the case of life threatening diseases), the benefits of administering a compound of the formula (0), (1) or (2) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a pulsatile or continuous manner.

The compound of formula (0), (1) or (2) will generally be administered to a subject in need of such administration, for example a human patient.

A typical daily dose of the compound can be up to 1000 mg per day, for example in the range from 0.01 milligrams to 10 milligrams per kilogram of body weight, more usually from 0.025 milligrams to 5 milligrams per kilogram of body weight, for example up to 3 milligrams per kilogram of bodyweight, and more typically 0.15 milligrams to 5 milligrams per kilogram of bodyweight although higher or lower doses may be administered where required.

By way of example, an initial starting dose of 12.5 mg may be administered 2 to 3 times a day. The dosage can be increased by 12.5 mg a day every 3 to 5 days until the maximal tolerated and effective dose is reached for the individual as determined by the physician. Ultimately, the quantity of compound administered will be commensurate with the nature of the disease or physiological condition being treated and the therapeutic benefits and the presence or absence of side effects produced by a given dosage regimen, and will be at the discretion of the physician.

The compounds of the formulae (0), (1) and (2) can be administered as the sole therapeutic agent or they can be administered in combination therapy with one of more other compounds such as steroids or interferons.

Methods of Diagnosis

Prior to administration of a compound of the formula (0), (1) or (2) a patient may be screened to determine whether a disease or condition from which the patient is or may be suffering is one which would be susceptible to treatment with a compound having activity against TYK2.

Accordingly, in further embodiments (3.1 to 3.6), the invention provides:

3.1 A compound as defined in any one of Embodiments 1.0 to 1.105 herein or any sub-groups or examples thereof as defined herein for use in the treatment or prophylaxis of a disease state or condition in a patient who has been screened and has been determined as suffering from, or being at risk of suffering from, a disease or condition which would be susceptible to treatment with a compound having activity against a TYK2 kinase.

3.2 The use of a compound as defined in any one of Embodiments 1.0 to 1.105 herein or any sub-groups or examples thereof as defined herein for the manufacture of a medicament for the treatment or prophylaxis of a disease state or condition in a patient who has been screened and has been determined as suffering from, or being at risk of suffering from, a disease or condition which would be susceptible to treatment with a compound having activity against TYK2 kinase.

3.3 A method for the diagnosis and treatment of a disease state or condition mediated by TYK2 kinase, which method comprises (i) screening a patient to determine whether a disease or condition from which the patient is or may be suffering is one which would be susceptible to treatment with a compound having activity against the kinase; and (ii) where it is indicated that the disease or condition from which the patient is thus susceptible, thereafter administering to the patient an effective TYK2 inhibiting amount of a compound as defined in any one of Embodiments 1.0 to 1.105 herein or any sub-groups or examples thereof as defined herein.

A subject (e.g. patient) may be subjected to a diagnostic test to detect a marker indicative of the presence of a disease or condition in which TYK2 is implicated, or a marker indicative of susceptibility to the said disease or condition. For example, subjects may be screened for genetic markers indicative of a susceptibility to develop an autoimmune or inflammatory disease.

The genetic marker can comprise a particular allele or single nucleotide polymorphism of the TYK2 gene which is indicative of susceptibility to an autoimmune disease such as multiple sclerosis (see for example Ban et al., *European Journal of Human Genetics* (2009), 17, 1309-1313) or an inflammatory bowel disease such as Crohn's disease (see Sato et al., *J. Clin. Immunol.* (2009), 29:815-825). The genetic marker can, for example, be a single nucleotide polymorphism in the TYK2 gene, or it can be a haplotype comprising a single nucleotide polymorphism in the TYK2 gene and a polymorphism in another gene.

The diagnostic tests are typically conducted on a biological sample selected from blood samples, biopsy samples, stool biopsies, sputum, chromosome analysis, pleural fluid, peritoneal fluid, or urine.

Methods of identifying genetic markers such as single nucleotide polymorphisms are well known. Examples of suitable methods for identifying such markers are described in Ban et al. and Sato et al. above.

EXAMPLES

The invention will now be illustrated, but not limited, by reference to the specific embodiments described in the following examples.

Enzyme Inhibition

Compounds of the invention were assayed for their ability to inhibit TYK2 kinase and other JAK kinases.

Substrates and kinases used in the assays are identified in Table 2 below.

Kinase assays were performed at Reaction Biology Corp., Malvern, Pa., USA, using the following general procedure:

1) Prepare indicated substrate in freshly prepared Base Reaction Buffer (20 mM Hepes pH 7.5, 10 mM $MgCl_2$, 1 mM EGTA, 0.02% Brij35, 0.02 mg/ml BSA, 0.1 mM $Na_3VO_4$, 2 mM DTT, 1% DMSO).

2) Deliver cofactors (1.5 mM $CaCl_2$, 16 ug/mL Calmodulin, 2 mM $MnCl_2$) to the substrate solution above 3) Deliver indicated kinase into the substrate solution and gently mix 4) Deliver varying concentrations of test compound in DMSO into the kinase reaction mixture 5) Deliver $^{33}$P-ATP (specific activity 0.01 µCi/µL final) into the reaction mixture to initiate the reaction 6) Incubate kinase reaction for 120 min at room temperature 7) Reactions are spotted onto P81 ion exchange filter paper (Whatman #3698-915)

8) Unbound phosphate is removed by washing filters extensively in 0.75% Phosphoric acid.

9) $^{33}$P signal was determined using Typhoon phosphorimagers (GE Healthcare). After subtraction of background derived from control reactions containing inactive enzyme, $IC_{50}$ values were determined using the nonlinear regression function in Prism (Graphpad software).

TABLE 2

| Protein Name | HUGO symbol | Substrate | Genbank Accession # | Protein Accession # | Clone | Expression | Tag |
|---|---|---|---|---|---|---|---|
| JAK1 | JAK1 | pEY | NP_002218.2 | P23458 | aa 866-1154 | Baculovirus in Sf21 insect cells | N-terminal GST tag |
| JAK2 | JAK2 | pEY | NP_004963 | O60674 | aa 809-1132 + g | Baculovirus in Sf21 insect cells | N-terminal GST tag |
| JAK3 | JAK3 | JAK3tide | NP_000206 | P52333 | aa 781-1124 | Baculovirus in Sf21 insect cells | N-terminal GST tag |
| TYK2 | TYK2 | AXLtide | NP_003322.2 | P29597 | Aa 833-1187 | Baculovirus in Sf21 insect cells | N-terminal GST tag |

Substrates:
AXLtide=[KKSRGDYMTMQIG]
JAK3tide=[Ac-GEEEEYFELVKKKK-$NH_2$]
pEY=poly Glu-Tyr [Glu:Tyr (4:1), M.W.=5,000–20,000]
The results are shown in Table 3 below.

TABLE 3

| Example Number (and method of preparation) | STRUCTURE | In Vitro Enzyme $IC_{50}$ (nM) | | | |
|---|---|---|---|---|---|
| | | TYK2 | JAK1 | JAK2 | JAK3 |
| Example 1 (Example Q-3 in WO2008/139161) | 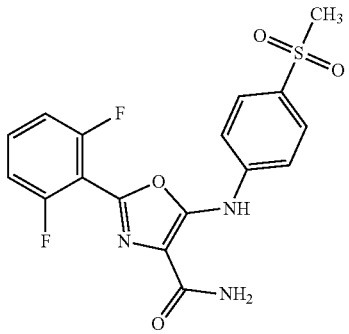 [SMILES: CS(=O)(=O)c1ccc(Nc2oc(-c3c(F)cccc3F)nc2C(N)=O)cc1] | 13.5 | 90.2 | 234.7 | 404.8 |

TABLE 3-continued

| Example Number (and method of preparation) | STRUCTURE | In Vitro Enzyme IC$_{50}$ (nM) | | | |
|---|---|---|---|---|---|
| | | TYK2 | JAK1 | JAK2 | JAK3 |
| Example 2 (Example Q-25 in WO2008/139161) | 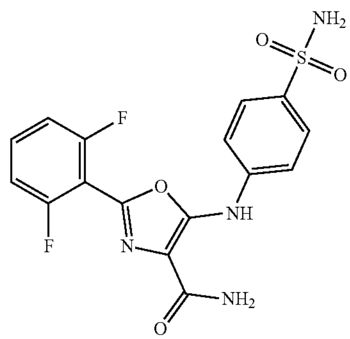 [SMILES: NC(=O)c1nc(-c2c(F)cccc2F)oc1Nc1ccc(S(N)(=O)=O)cc1] | 14.6 | 78.2 | 146.6 | 418.8 |
| Example 3 (Example Q-26 in WO2008/139161) | 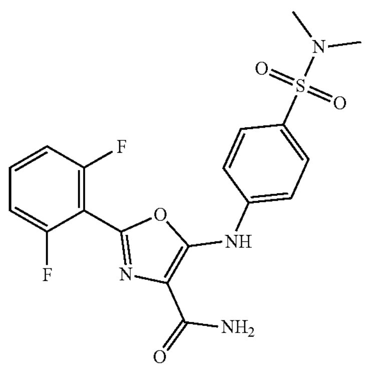 [SMILES: CN(C)S(=O)(=O)c1ccc(Nc2oc(-c3c(F)cccc3F)nc2C(N)=O)cc1] | 5.3 | 47.6 | 95.0 | 359.0 |
| Example 4 (Example Q-27 in WO2008/139161) | 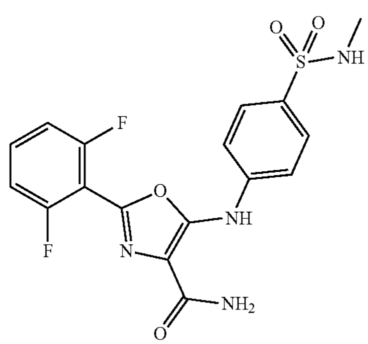 [SMILES: CNS(=O)(=O)c1ccc(Nc2oc(-c3c(F)cccc3F)nc2C(N)=O)cc1] | 13.8 | 65.6 | 109.0 | 387.2 |
| Example 5 (Example Q-20 in WO2008/139161) | 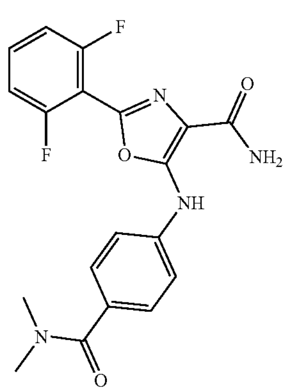 [SMILES: CN(C)C(=O)c1ccc(Nc2oc(-c3c(F)cccc3F)nc2C(N)=O)cc1] | 9.2 | 88.6 | 112.1 | 218.9 |

TABLE 3-continued

| Example Number (and method of preparation) | STRUCTURE | In Vitro Enzyme IC$_{50}$ (nM) | | | |
|---|---|---|---|---|---|
| | | TYK2 | JAK1 | JAK2 | JAK3 |
| Example 6 (Example Q-51 in WO2008/139161) | 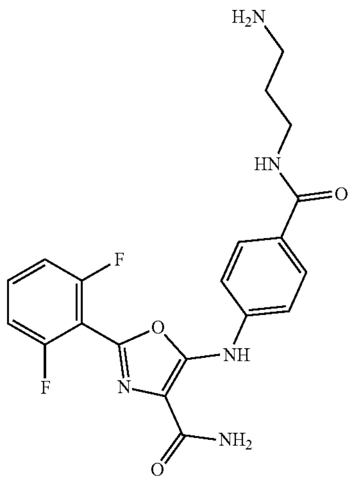 [SMILES: NCCCNC(=O)c1ccc(Nc2oc(-c3c(F)cccc3F)nc2C(N)=O)cc1] | 25.0 | 192.4 | 297.1 | 471.6 |
| Example 7 (Example Q-54 in WO2008/139161) | 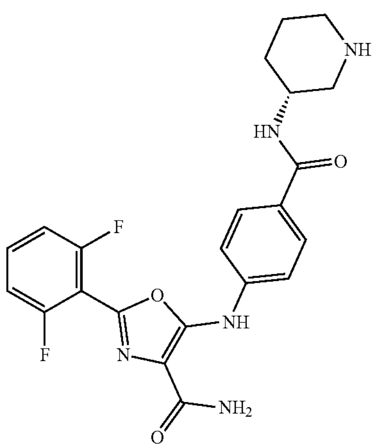 [SMILES: NC(=O)c1nc(-c2c(F)cccc2F)oc1Nc1ccc(C(=O)N[C@@H]2CCCNC2)cc1] | 9.8 | 201.5 | 261.0 | 419.3 |
| Example 8 (Example Q-53 in WO2008/139161) | 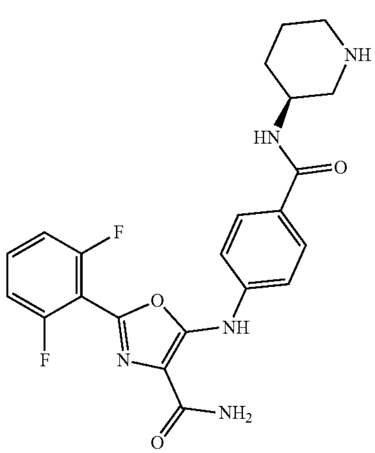 [SMILES: NC(=O)c1nc(-c2c(F)cccc2F)oc1Nc1ccc(C(=O)N[C@H]2CCCNC2)cc1] | 12.9 | 201.0 | 267.5 | 408.5 |

TABLE 3-continued
| Example Number (and method of preparation) | STRUCTURE | In Vitro Enzyme IC$_{50}$ (nM) | | | |
|---|---|---|---|---|---|
| | | TYK2 | JAK1 | JAK2 | JAK3 |
| Example 9 (Example U-2 in WO2008/139161) | 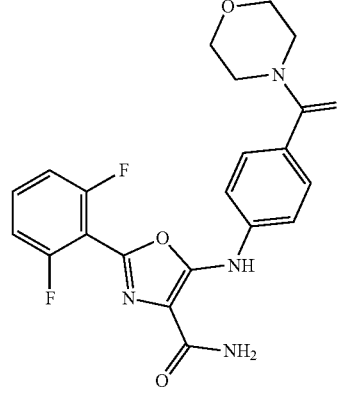 | 22.7 | 75.6 | 267.4 | 423.4 |
| Example 10 (Example U-3 in WO2008/139161) | 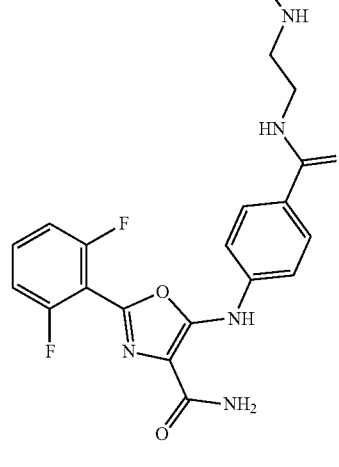 | 20.5 | 183.3 | 311.4 | 397.2 |
| Example 11 (Example U-4 in WO2008/139161) | 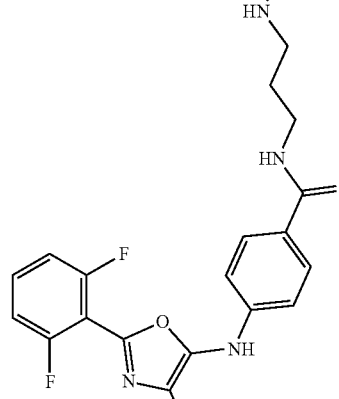 | 15.1 | 189.6 | 338.4 | 387.7 |

TABLE 3-continued

| Example Number (and method of preparation) | STRUCTURE | In Vitro Enzyme IC$_{50}$ (nM) | | | |
|---|---|---|---|---|---|
| | | TYK2 | JAK1 | JAK2 | JAK3 |
| Example 12 (Example U-6 in WO2008/139161) | 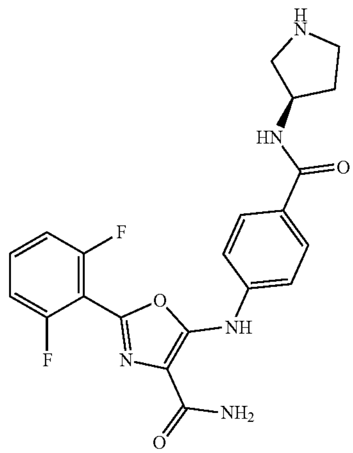 [SMILES: NC(=O)c1nc(-c2c(F)cccc2F)oc1Nc1ccc(C(=O)N[C@@H]2CCNC2)cc1] | 23.41 | 168.6 | 292.4 | 346.2 |
| Example 13 (Example U-7 in WO2008/139161) | 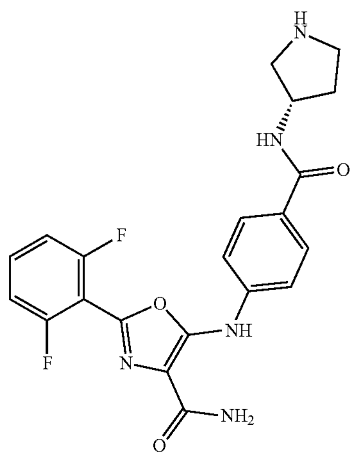 [SMILES: NC(=O)c1nc(-c2c(F)cccc2F)oc1Nc1ccc(C(=O)N[C@H]2CCNC2)cc1] | 11.2 | 123.0 | 181.6 | 341.5 |
| Example 14 (Example U-12 in WO2008/139161) | 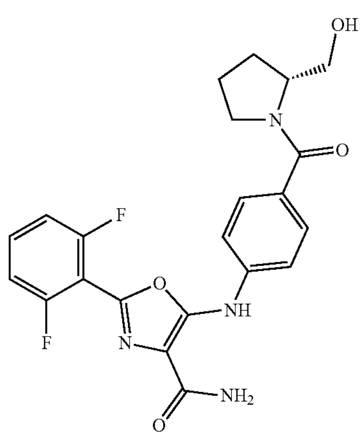 [SMILES: NC(=O)c1nc(-c2c(F)cccc2F)oc1Nc1ccc(C(=O)N2CCC[C@@H]2CO)cc1] | 9.6 | 67.22 | 36.0 | 125.9 |

TABLE 3-continued
| Example Number (and method of preparation) | STRUCTURE | In Vitro Enzyme IC$_{50}$ (nM) | | | |
|---|---|---|---|---|---|
| | | TYK2 | JAK1 | JAK2 | JAK3 |
| Example 15 (Example U-16 in WO2008/139161) | 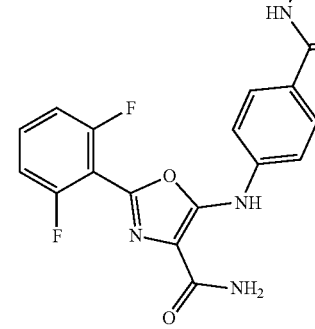 | 7.5 | 41.1 | 101.3 | 194.9 |
| Example 16 (Example U-17 in WO2008/139161) | 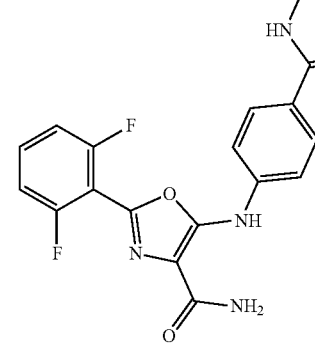 | 8.4 | 58.1 | 118.8 | 199.1 |
| Example 17 (Example U-21 in WO2008/139161) | 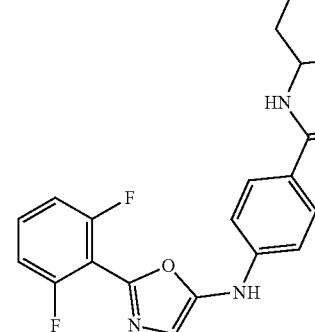 | 13.7 | 152.8 | 167.2 | 99.2 |

TABLE 3-continued

| Example Number (and method of preparation) | STRUCTURE | In Vitro Enzyme IC$_{50}$ (nM) | | | |
|---|---|---|---|---|---|
| | | TYK2 | JAK1 | JAK2 | JAK3 |
| Example 18 (Example U-18 in WO2008/139161) | [structure] | 13.8 | 118.3 | 191.8 | 164.6 |

The data set out in the table above illustrate that compounds of formula (1) are potent inhibitors of TYK2 kinase and show a pronounced selectivity for TYK2 kinase compared to other JAK kinases.

On the basis of their activity against TYK2 kinase, it is envisaged that the compounds of the formula (1) will be useful as therapeutic agents for treating a wide range of inflammatory, immunological and allergic diseases and conditions.

Examples 19 to 33

The compounds of Examples 19 to 33 in Table 4 below are novel compounds and are made using the methods described below or methods analogous thereto. The starting materials and synthetic intermediates used in the methods are shown in Table 5 and the NMR and LCMS properties of the final products are set out in Table 6.

TABLE 4

Example 19 [structure]

TABLE 4-continued

Example 20 [structure]

Example 21 [structure]

TABLE 4-continued
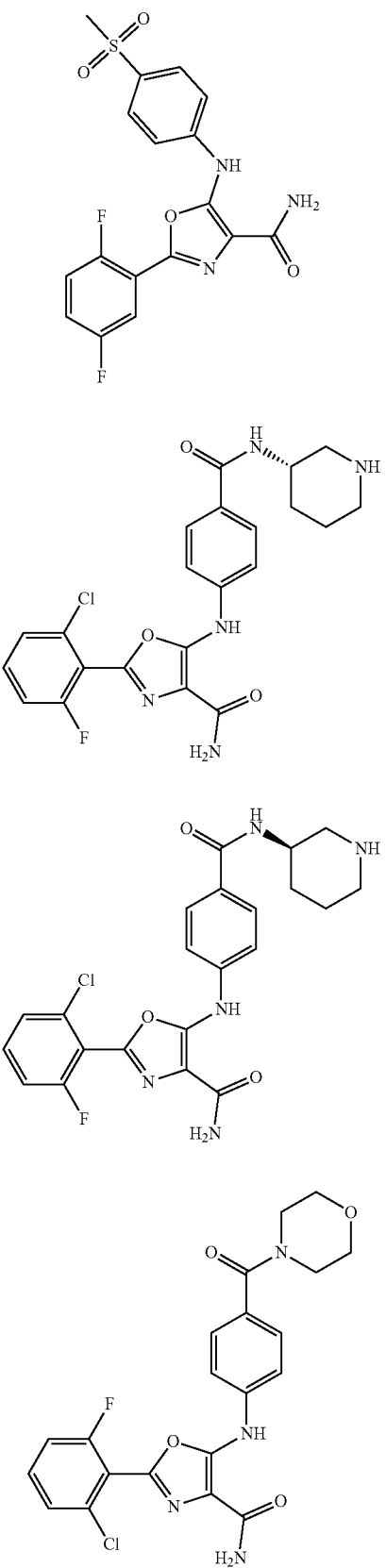
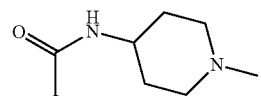
Example 26
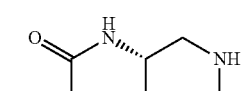
Example 27
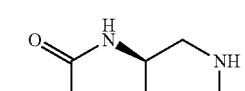
Example 28
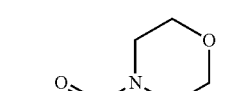
Example 29

TABLE 4-continued

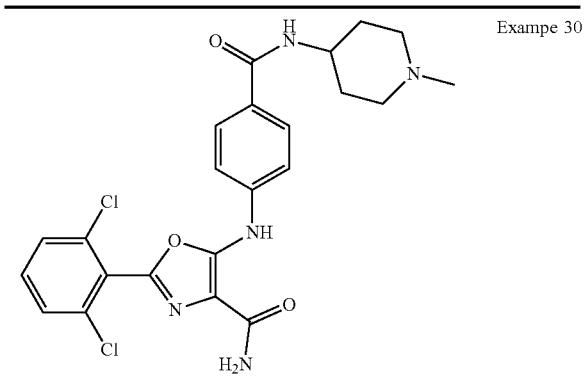

Example 30

Example 31

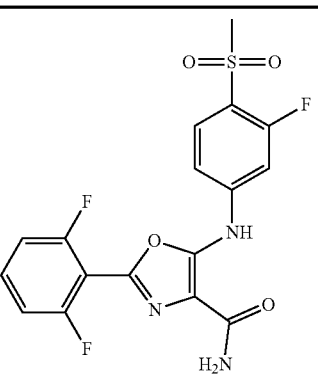

Example 32

Example 33

TABLE 5

Synthetic Intermediates and Starting Materials

| Compound | Structure | Source or method of preparation |
|---|---|---|
| I-1 | 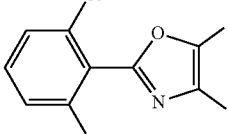 | Prepared as described in steps a and b from Example F-1 in WO2008/139161, using 2,6-dichlorobenzoyl chloride in step a |
| I-2 | 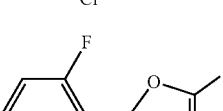 | Prepared as described in steps a and b from Example F-1 in WO2008/139161, using 2-chloro-6-fluorobenzoyl chloride in step a |
| I-3 | 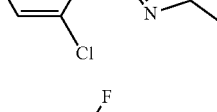 | Prepared as described in steps a and b from Example F-1 in WO2008/139161, using 2,4,6-trifluorobenzoyl chloride in step a |
| I-4 | 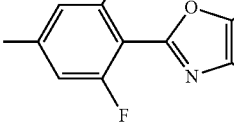 | Prepared as described in steps a and b from Example F-1 in WO2008/139161, using 2,5-difluorobenzoyl chloride in step a |

TABLE 5-continued

Synthetic Intermediates and Starting Materials

| Compound | Structure | Source or method of preparation |
|---|---|---|
| I-5 | [Structure: 2-(2,6-difluorophenyl)-5-bromo-4-cyanooxazole] | Example F-1 of WO2008/139161 |
| I-6 | [Structure: 4-(methylsulfonyl)aniline] | Commercially available |
| I-7 | [Structure: 4-(ethylsulfonyl)aniline] | Commercially available |
| I-8 | [Structure: 4-(isopropylsulfonyl)aniline] | Commercially available |
| I-9 | [Structure: 3-fluoro-4-(methylsulfonyl)aniline] | Commercially available |
| I-10 | [Structure: methyl 4-aminobenzoate] (Compound (13) in General Method B) | Commercially available |
| I-11 | [Structure: (R)-tert-butyl 3-aminopiperidine-1-carboxylate] | Commercially available |
| I-12 | [Structure: (S)-tert-butyl 3-aminopiperidine-1-carboxylate] | Commercially available |
| I-13 | [Structure: 4-amino-1-methylpiperidine] | Commercially available |

General Method a

Step a—Preparation of Intermediate Compound (12)

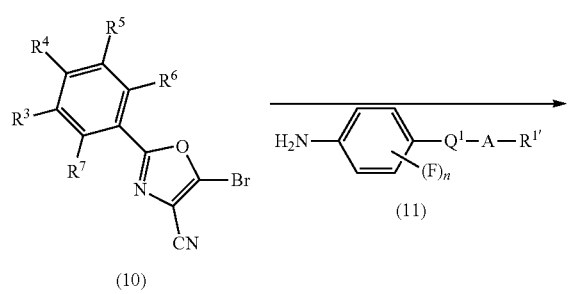

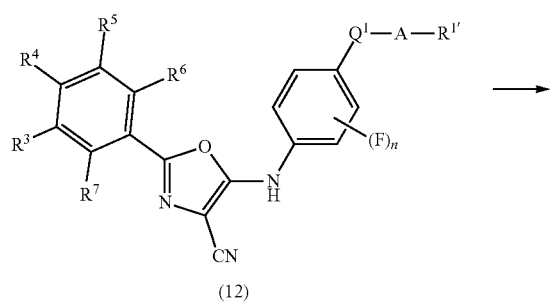

In the reaction scheme, the group $R^{1'}$ in formulae (11) and (12) is either a group $R^1$ as defined herein or a protected form of the group $R^1$.

A solution of palladium acetate (0.025 mmol) and (±)-2,2"-bis(diphenylphosphino)-1,1"-binaphthalene (0.024 mmol) in DMF (7.1 mL) is stirred at room temperature for 3 minutes. Then compound (10) (0.35 mmol), compound (11) (1.40 mmol) and potassium phosphate tribasic (0.70 mmol) are added and the mixture heated in the microwave for 3 minutes at 180° C. The reaction is diluted with EtOAc and washed with water. The organic phase is passed through a MP-SH resin cartridge, dried over $MgSO_4$ and the solvent removed in vacuo. The residue is purified by silica gel column chromatography using a gradient 10-100% EtOAc in hexanes to afford Compound (12), the identity of which can be confirmed by $^1H$ NMR (DMSO) and LCMS.

Step b—Preparation of Compound (2)

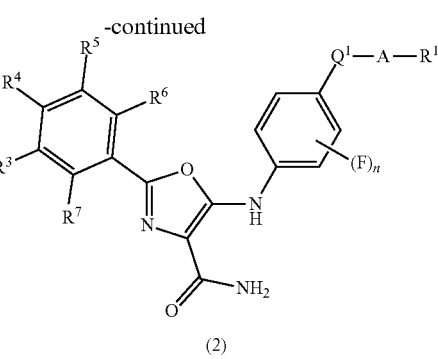

A solution of Compound (12) (0.09 mmol) in concentrated sulfuric acid (1.7 mL) is stirred at room temperature for 1.5 hours. The solution is neutralised by pouring into saturated sodium bicarbonate solution. The aqueous phase is extracted with EtOAc. The combined organic phase is dried over $MgSO_4$ and the solvent is removed in vacuo to afford Compound (2), the identity of which can be confirmed by $^1H$ NMR (DMSO) and LCMS.

General Method B

Step a—Preparation of Intermediate Compound (14)

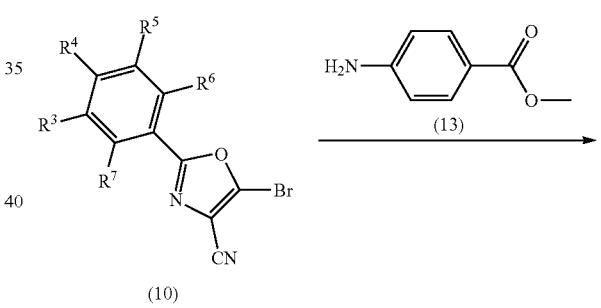

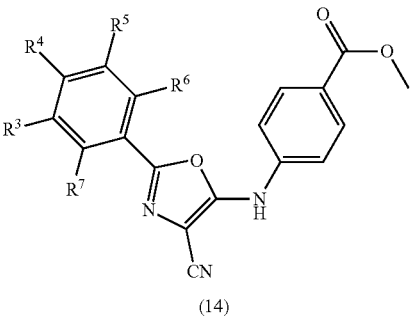

Compound (10) is reacted with compound (13) under the conditions set out in step a of General Method A to give Compound (14).

Step b—Preparation of Intermediate Compound (15)

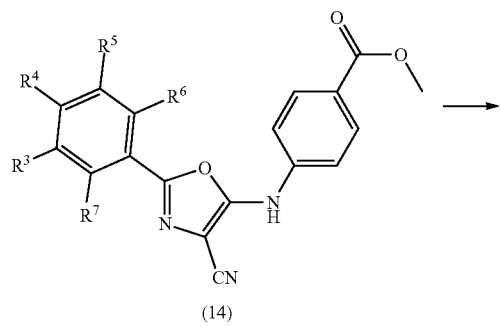

(14)

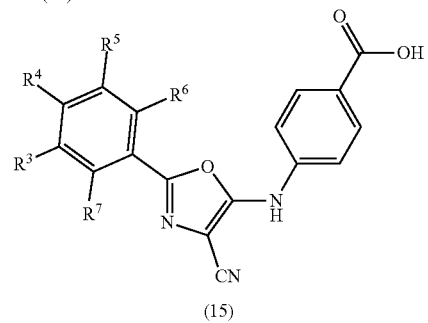

(15)

Compound (14) is hydrolysed using lithium hydroxide to give the carboxylic acid Compound (15).

Alternatively, Compound (15) can be prepared by the method of step a of Example U-1 of WO2008/139161 or methods analogous thereto.

Step c—Preparation of Intermediate Compound (16)

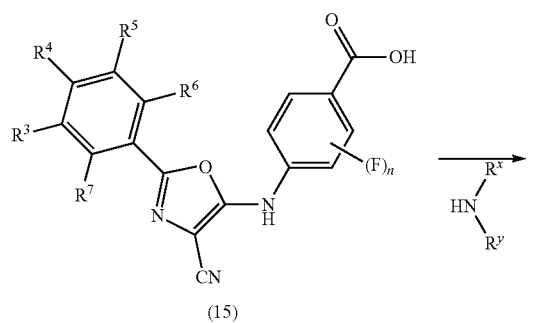

(15)

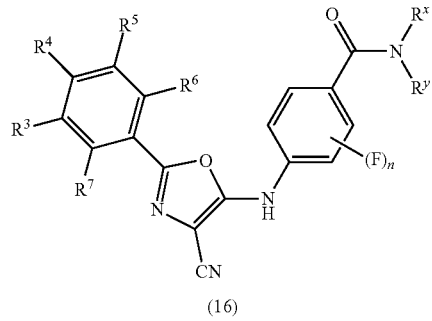

(16)

To a solution of Compound (15) (0.059 mmol), O-(7-azabenzotriazol-1-yl)-N,N,N',N'-tetramethyluronium hexafluorophosphate (0.059 mmol), and diisopropylethylamine (0.117 mmol) in N,N-dimethylformamide (2 mL) is added an amine of formula HNR$^x$R$^y$ (0.059 mmol) and the reaction mixture is stirred at room temperature for 16 hours. The reaction mixture is then diluted with EtOAc washed with 1M HCl, water and brine. The organic phase is dried over MgSO$_4$ and the solvent removed in vacuo. The residue is purified by preparative HPLC to afford Compound (16), the identity of which can be confirmed by LCMS.

Step d—Preparation of Compound (17)

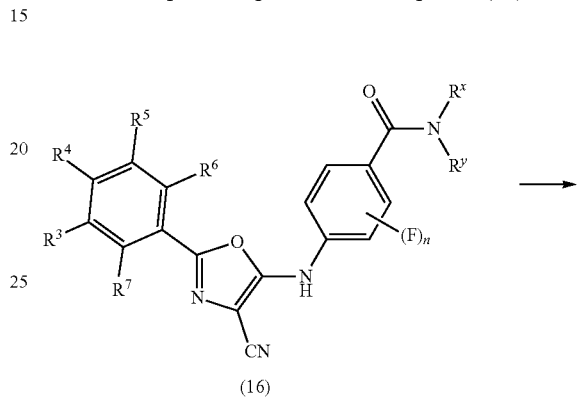

(16)

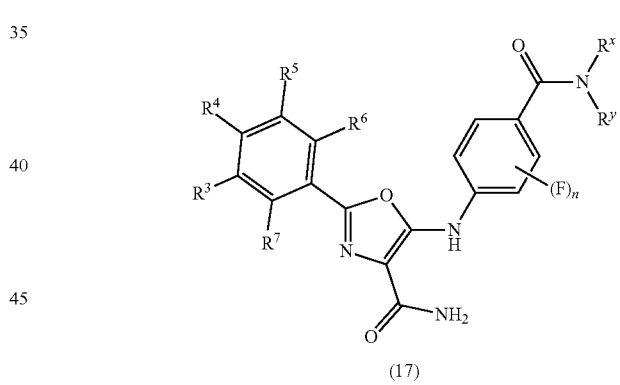

(17)

A solution of Compound (16) (0.022 mmol) in concentrated sulfuric acid (0.5 mL) is stirred at room temperature for 1.5 hours. The solution is neutralised by pouring into saturated sodium bicarbonate solution. The aqueous phase is then basified to pH14 using 5M NaOH and extracted with EtOAc. The combined organic phase is dried over MgSO$_4$ and the solvent removed in vacuo to afford Compound (17), the identity of which can be confirmed by $^1$H NMR (DMSO) and LCMS. Compounds (17) containing a basic nitrogen, such as those prepared from I-11 or I-12 which bear an acid-sensitive nitrogen protecting group, are concomitantly deprotected during the final acid-mediated reaction step.

General Method B can be used to make compounds wherein NR$^x$R$^y$ forms a cyclic amine such as a morpholino, piperazino or piperidino group or compounds wherein R$^x$ is hydrogen or a substituent and R$^y$ is hydrogen or a substituent.

TABLE 6

| Ex. No. | Name | Synthetic method | ¹H NMR | LCMS |
|---|---|---|---|---|
| 19 | 2-(2,6-Dichloro-phenyl)-5-(4-methanesulfonyl-phenylamino)-oxazole-4-carboxylic acid amide | General Method A using intermediates I-1 and I-6. | (DMSO) δ 9.86 (1H, s), 7.83 (2H, d), 7.73-7.65 (4H, m), 7.48 (3H, d), 3.14 (3H, s) | m/z (ES+) 426 |
| 20 | 2-(2-Chloro-6-fluoro-phenyl)-5-(4-methanesulfonyl-phenylamino)-oxazole-4-carboxylic acid amide | General Method A using intermediates I-2 and I-6. | (DMSO) δ 9.86 (1H, s), 7.83 (2H, d), 7.64 (1H, q), 7.58-7.48 (6H, m), 3.16 (3H, s) | m/z (ES+) 410 |
| 21 | 5-(4-Methanesulfonyl-phenylamino)-2-(2,4,6-trifluoro-phenyl)-oxazole-4-carboxylic acid amide | General Method A using intermediates I-3 and I-6. | (DMSO) δ 9.81 (1H, s), 7.81 (2H, d), 7.54 (2H, d), 7.46-7.44 (4H, m), 3.15 (3H, s) | m/z (ES+) 412 |
| 22 | 2-(2,5-Difluoro-phenyl)-5-(4-methanesulfonyl-phenylamino)-oxazole-4-carboxylic acid amide | General Method A using intermediates I-4 and I-6. | (DMSO) δ 9.84 (1H, s), 7.85 (2H, d), 7.78 (1H, br. s), 7.63 (2H, d), 7.51-7.45 (4H, m), 3.19 (3H, s) | m/z (ES+) 394 |
| 23 | (S) 2-(2-Chloro-6-fluoro-phenyl)-5-[4-(piperidin-3-ylcarbamoyl)-phenylamino]-oxazole-4-carboxylic acid amide | General Method B using intermediates I-2, I-10 and I-11 | | |
| 24 | (R) 2-(2-Chloro-6-fluoro-phenyl)-5-[4-(piperidin-3-ylcarbamoyl)-phenylamino]-oxazole-4-carboxylic acid amide | General Method B using intermediates I-2, I-10 and I-12 | (MeOD) δ 7.87 (2H, d), 7.62-7.59 (1H, m), 7.49-7.46 (3H, m), 7.33 (1H, t), 4.29-4.24 (1H, m), 3.53 (1H, dd), 3.39-3.35 (1H, m), 3.02-2.92 (2H, m), 2.13-2.07 (2H, m), 1.89-1.74 (2H, m) | m/z (ES+) 458 |
| 25 | 2-(2-Chloro-6-fluoro-phenyl)-5-[4-(morpholine-4-carbonyl)-phenylamino]-oxazole-4-carboxylic acid amide | General Method B using intermediates I-2, I-10 and morpholine | (DMSO) δ 9.50 (1H, s), 7.64 (1H, dd), 7.54 (1H, d), 7.47-7.45 (2H, m), 7.39-7.34 (5H, m), 3.55 (4H, br. m), 3.36 (4H, br. m) | m/z (ES+) 445 |
| 26 | 2-(2-Chloro-6-fluoro-phenyl)-5-[4-(1-methyl-piperidin-4-ylcarbamoyl)-phenylamino]-oxazole-4-carboxylic acid amide | General Method B using intermediates I-2, I-10 and I-13 | (MeOD) δ 7.87 (2H, d), 7.62-7.58 (1H, m), 7.51-7.47 (3H, m), 7.34 (1H, t), 4.16 (1H, m), 3.59 (2H, m), 3.20 (2H, m), 2.92 (3H, s), 2.24 (2H, m), 1.92 (2H, m) | m/z (ES+) 472 |
| 27 | (S) 2-(2,6-Dichloro-phenyl)-5-[4-(piperidin-3-ylcarbamoyl)-phenylamino]-oxazole-4-carboxylic acid amide | General Method B using intermediates I-1, I-10 and I-11 | (MeOD) δ 7.82 (2H, d), 7.59-7.52 (3H, m), 7.40 (2H, d), 4.23-4.18 (1H, m), 3.49 (1H, dd), 3.34-3.29 (1H, m), 2.97-2.86 (2H, m), 2.09-2.03 (2H, m) 1.84-1.69 (2H, m) | m/z (ES+) 474 |
| 28 | (R) 2-(2,6-Dichloro-phenyl)-5-[4-(piperidin-3-ylcarbamoyl)-phenylamino]-oxazole-4-carboxylic acid amide | General Method B using intermediates I-1, I-10 and I-12 | (MeOD) δ 7.86 (2H, d), 7.64-7.60 (3H, m), 7.44 (2H, d), 4.25-4.23 (1H, m), 3.52 (1H, dd), 3.38-3.33 (1H, m), 3.02-2.90 (2H, m), 2.11-2.07 (2H, m) 1.88-1.74 (2H, m) | m/z (ES+) 474 |
| 29 | 2-(2,6-Dichloro-phenyl)-5-[4-(morpholine-4-carbonyl)-phenylamino]-oxazole-4-carboxylic acid amide | General Method B using intermediates I-1, I-10 and morpholine | | |
| 30 | 2-(2,6-Dichloro-phenyl)-5-[4-(1-methyl-piperidin-4-ylcarbamoyl)-phenylamino]-oxazole-4-carboxylic acid amide | General Method B using intermediates I-1, I-10 and I-13 | (MeOD) δ 7.85 (2H, d), 7.62-7.59 (3H, m), 7.43 (2H, d), 4.15 (1H, m), 3.58 (2H, m), 3.19 (2H, m), 2.91 (3H, s), 2.22 (2H, m), 1.93 (2H, m) | m/z (ES+) 490 |
| 31 | 2-(2,6-Difluoro-phenyl)-5-(4-ethanesulfonyl-phenylamino)-oxazole-4-carboxylic acid amide | General Method A using intermediates I-5 and I-7. | (DMSO) δ 9.82 (1H, s), 7.74 (2H, d), 7.62-7.60 (1H, m), 7.54 (2H, d), 7.44 (2H, br s), 7.33-7.29 (2H, m), 3.20 (2H, q), 1.06 (3H, t) | m/z (ES+) 430 (M + Na⁺) |
| 32 | 2-(2,6-Difluoro-phenyl)-5-(4-methanesulfonyl-phenylamino)-oxazole-4-carboxylic acid amide | General Method A using intermediates I-5 and I-6. | (DMSO) δ 10.07 (1H, s), 7.73-7.67 (2H, m), 7.52-7.45 (3H, m), 7.40-7.34 (3H, m), 3.27 (3H, s) | m/z (ES+) 434 (M + Na⁺) |
| 33 | 2-(2,6-Difluoro-phenyl)-5[4-propane-2-sulfonyl)-phenylamino]-oxazole-4-carboxylic acid amide | General Method A using intermediates I-5 and I-8. | (DMSO) δ 9.83 (1H, s), 7.71 (2H, d), 7.63-7.60 (1H, m), 7.54 (2H, d), 7.44 (2H, br s), 7.33-7.29 (2H, m), 3.35 (1H, m), 1.11 (6H, d) | m/z (ES+) 444 (M + Na⁺) |

Example 34

Enzyme Inhibitory Activities of Novel Compounds of Formula (2)

Novel compounds of formula (2) were tested in the TYK2 kinase inhibition assay and the other JAK kinase inhibition assays described above. The results are shown in Table 7 below.

TABLE 7

| Compound of Example No. | In Vitro Enzyme $IC_{50}$ (nM) | | | |
|---|---|---|---|---|
| | TYK2 | JAK1 | JAK2 | JAK3 |
| 19 | 2.3 | 21.9 | 87.7 | 214 |
| 20 | 2.7 | 28.7 | 72.6 | 165 |
| 21 | 68.3 | 241 | 412 | 2180 |
| 22 | 183 | 843 | 663 | 5500 |

Example 35

Pharmaceutical Formulations (i) Tablet Formulation

A tablet composition containing a compound of the formula (0), (1) or (2) is prepared by mixing 50 mg of the compound with 197 mg of lactose (BP) as diluent, and 3 mg magnesium stearate as a lubricant and compressing to form a tablet in a known manner.

(ii) Capsule Formulation

A capsule formulation is prepared by mixing 100 mg of a compound of the formula (0), (1) or (2) with 100 mg lactose and filling the resulting mixture into standard opaque hard gelatin capsules.

(iii) Injectable Formulation I

A parenteral composition for administration by injection can be prepared by dissolving a compound of the formula (0), (1) or (2) (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formula (0), (1) or (2) (e.g. in salt form) (2 mg/mL) and mannitol (50 mg/mL), sterile filtering the solution and filling into sealable 1 mL vials or ampoules.

(iv) Sub-Cutaneous Injection Formulation

A composition for sub-cutaneous administration is prepared by mixing a compound of the formula (0), (1) or (2) with pharmaceutical grade corn oil to give a concentration of 5 mg/mL. The composition is sterilised and filled into a suitable container.

Equivalents

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A method of treating a disease or condition in a subject in need thereof, wherein the disease is selected from an autoimmune disease, an inflammatory disease or condition, an immunological disease or condition, an allergic disease or disorder, a transplant rejection and Graft-versus host disease, or a disease or condition selected from sepsis and septic shock, wherein the disease or condition is susceptible to TYK2 inhibition, which method comprises inhibiting a TYK2 kinase by administering to the subject an effective TYK2 kinase-inhibiting amount of 2-(2,6-dichloro-phenyl)-5-[4-(morpholine-4-carbonyl)-phenylamino]-oxazole-4-carboxylic acid amide or a salt thereof.

2. The method of claim 1 wherein the disease or condition is an autoimmune disease.

3. A method according to claim 2 wherein the autoimmune disease is psoriasis.

4. A method according to claim 2 wherein the autoimmune disease is multiple sclerosis.

5. A method according to claim 1 wherein the disease or condition is an inflammatory disease or condition.

6. A method according to claim 1 wherein the disease or condition is an immunological disease or condition.

7. A method according to claim 1 wherein the disease or condition is an allergic disease or disorder.

8. A method according to claim 1 wherein the disease or condition is a transplant rejection.

9. A method according to claim 1 wherein the disease or condition is Graft-versus host disease.

10. A method according to claim 1 wherein the disease or condition is selected from sepsis and septic shock.

11. A method according to claim 1 wherein the disease or condition is selected from:
    (a) skin inflammation due to radiation exposure;
    (b) asthma;
    (c) allergic inflammation;
    (d) chronic inflammation;
    (e) an inflammatory ophthalmic disease;
    (f) dry eye syndrome;
    (g) uveitis;
    (h) insulin-dependent diabetes;
    (i) Hashimoto's thyroiditis;
    (j) Graves' disease;
    (k) Cushing's disease;
    (l) Addison's disease
    (m) chronic active hepatitis;
    (n) polycystic ovary syndrome;
    (o) coeliac disease;
    (p) psoriasis;
    (q) inflammatory bowel disease;
    (r) ankylosing spondylitis;
    (s) rheumatoid arthritis;
    (t) systemic lupus erythematosus;
    (u) myasthenia gravis;
    (v) transplant rejection; and
    (w) graft-versus-host disease.

12. A method according to claim 1 wherein the disease or condition is rheumatoid arthritis.

13. A method according to claim 1 wherein the disease or condition is inflammatory bowel disease.

14. A method according to claim 1 wherein the subject is a patient who has been screened and has been determined as suffering from a disease or condition which would be susceptible to treatment with a compound having activity against a TYK2 kinase.

15. A method according to claim 2 wherein the subject is a patient who has been screened and has been determined as suffering from a disease or condition which would be susceptible to treatment with a compound having activity against a TYK2 kinase.

16. A method according to claim 3 wherein the subject is a patient who has been screened and has been determined as suffering from a disease or condition which would be susceptible to treatment with a compound having activity against a TYK2 kinase.

17. A method according to claim 4 wherein the subject is a patient who has been screened and has been determined as suffering from a disease or condition which would be susceptible to treatment with a compound having activity against a TYK2 kinase.

18. A method according to claim 5 wherein the subject is a patient who has been screened and has been determined as suffering from a disease or condition which would be susceptible to treatment with a compound having activity against a TYK2 kinase.

19. A method according to claim 6 wherein the subject is a patient who has been screened and has been determined as suffering from a disease or condition which would be susceptible to treatment with a compound having activity against a TYK2 kinase.

20. A method according to claim 11 wherein the subject is a patient who has been screened and has been determined as suffering from a disease or condition which would be susceptible to treatment with a compound having activity against a TYK2 kinase.

\* \* \* \* \*